United States Patent
Kikuchi

(10) Patent No.: US 10,440,290 B2
(45) Date of Patent: Oct. 8, 2019

(54) RADIOGRAPHIC IMAGE CAPTURING APPARATUS AND RADIOGRAPHIC IMAGE CAPTURING SYSTEM

(71) Applicant: Konica Minolta, Inc., Chiyoda-ku, Tokyo (JP)

(72) Inventor: Ryouhei Kikuchi, Hachioji (JP)

(73) Assignee: KONICA MINOLTA, INC., Chiyoda-Ku, Tokyo (JP)

( * ) Notice: Subject to any disclaimer, the term of this patent is extended or adjusted under 35 U.S.C. 154(b) by 244 days.

(21) Appl. No.: 15/479,817

(22) Filed: Apr. 5, 2017

(65) Prior Publication Data

US 2017/0290558 A1    Oct. 12, 2017

(30) Foreign Application Priority Data

Apr. 8, 2016    (JP) .................... 2016-077887

(51) Int. Cl.
  *A61B 6/00*    (2006.01)
  *H04N 5/32*    (2006.01)

(52) U.S. Cl.
  CPC .............. *H04N 5/32* (2013.01); *A61B 6/4233* (2013.01); *A61B 6/4283* (2013.01)

(58) Field of Classification Search
  CPC ......... A61B 6/00; A61B 6/586; A61B 6/4283; A61B 6/44; A61B 6/4405; A61B 6/58; H05G 1/56

USPC ................. 378/98.8, 114, 117, 207
See application file for complete search history.

(56) References Cited

U.S. PATENT DOCUMENTS 9,250,335 B2 *   2/2016   Okada .................. G01T 1/2928
9,265,476 B2 *   2/2016   Iwakiri ................ A61B 6/4233

FOREIGN PATENT DOCUMENTS

JP    2011067334 A    4/2011
JP    2012049665 A    3/2012

* cited by examiner

*Primary Examiner* — Jurie Yun
(74) *Attorney, Agent, or Firm* — Cantor Colburn LLP

(57) ABSTRACT

A radiographic image capturing apparatus, includes the following. A sensor panel includes scanning lines, signal lines, a two-dimensional array of radiation detecting elements each having a first electrode and a second electrode, bias lines each applying a reverse bias voltage to the corresponding radiation detecting element, and switching elements. The first electrode of each radiation detecting element is connected to the corresponding bias line. The second electrode of the radiation detecting element is connected to the corresponding signal line via the corresponding switch element. A determination unit determines any defect in the sensor panel based on a signal value read after varying a potential difference between each signal line and the corresponding bias line or a signal value read after turning-on or turning-off of each switching element during a readout operation from the corresponding radiation detecting element.

11 Claims, 13 Drawing Sheets

RADIOGRAPHIC IMAGE CAPTURING APPARATUS AND RADIOGRAPHIC IMAGE CAPTURING SYSTEM

CROSS REFERENCE TO RELATED APPLICATIONS

The present invention claims priority under 35 U.S.C. § 119 to Japanese Application No. 2016-077887 filed Apr. 8, 2016, the entire content of which is incorporated herein by reference.

BACKGROUND OF THE INVENTION

Field of the Invention

The present invention relates to radiographic image capturing apparatuses and radiographic image capturing systems.

Description of Related Art

A variety of radiographic image capturing apparatuses have been developed that generate electric charges at radiation detecting elements in proportion to the dose of emitted radiation and read the generated electric charges in the form of image data. These radiographic image capturing apparatuses are known as flat panel detectors (FPDs). Traditional radiographic image capturing apparatuses are of a dedicated (stationary) type and integrated with their holders. Recently, radiographic image capturing apparatuses of portable type (also referred to as "cassette type") have been developed and put into practical use, each including radiation detecting elements accommodated in a housing (For example, refer to Japanese Unexamined Patent Application Publication No. 2012-49665).

In many cases, such a radiographic image capturing apparatus includes a two-dimensional array (matrix) of radiation detecting elements 7 on a sensor board 4 which constitutes a sensor panel SP, as shown in, for example, FIG. 3 (described below). The sensor board 4 is provided with various lines, such as scanning lines 5, signal lines 6 and bias lines 9 thereon. Thin film transistors (TFTs) 8 are also provided thereon to function as switching elements to accumulate signal electric charges in the radiation detecting elements 7 or release the accumulated signal electric charges from the radiation detecting elements 7. The scanning lines 5 are capable of selectively applying a voltage to accumulate signal electric charges in the TFTs 8 ("off-voltage") and a voltage to release the accumulated electric charges from the TFTs 8 ("on-voltage").

Any impact applied to a portable radiographic image capturing apparatus when the apparatus is dropped or hit against other objects may cause disconnection in the scanning lines, signal lines or bias lines, resulting in malfunction of the sensor panel SP. More specifically, image data can no longer be read from the radiation detecting elements or abnormal image data is read.

To avoid such a situation, Japanese Unexamined Patent Application Publication No. 2011-67334, for example, discloses a radiographic image capturing apparatus capable of self-diagnosing the possibility of any defect in a sensor panel (or the radiographic image capturing apparatus) when the radiographic image capturing apparatus detects an impact. More specifically, the radiographic image capturing apparatus captures images while no radiation is emitted thereto, reads an offset image (image captured while no radiation is exposed to a subject), and analyzes the read offset image to determine the possibility of any defect in the sensor panel (or the radiographic image capturing apparatus).

The method disclosed in Japanese Unexamined Patent Application Publication No. 2011-67334 analyzes, for example, the pixel value of, the noise level of, and point and line defects in the offset image captured based on dark electric charges (also referred to as "dark current") generated in the radiation detecting elements, to determine any defect. Unfortunately, the offset image, which is captured while no radiation is emitted to the radiographic image capturing apparatus, as described above, has a significantly small data density (almost zero).

Accordingly, the analysis of such an offset image does not lead to an accurate detection of disconnection in, for example, the signal lines 6 or the bias lines 9. The research of the inventors of the present invention has revealed that the above method has a difficulty in detecting any disconnection in the scanning lines 5, which apply an on-voltage or off-voltage to the TFTs 8 (switching elements) to turn them on or off.

BRIEF SUMMARY OF THE INVENTION

An object of the present invention, which has been made in view of the problems described above, is to provide a radiographic image capturing apparatus and a radiographic image capturing system capable of properly and accurately determining the possibility of any defect in the sensor panel due to disconnection of any line in the radiographic image capturing apparatus.

According to one aspect of the present invention, there is provided a radiographic image capturing apparatus, including: a sensor panel including scanning lines, signal lines, a two-dimensional array of radiation detecting elements each having a first electrode and a second electrode, bias lines each applying a reverse bias voltage to the corresponding radiation detecting element, and switching elements, the first electrode of each radiation detecting element being connected to the corresponding bias line, the second electrode of the radiation detecting element being connected to the corresponding signal line via the corresponding switch element; and a determination unit determining any defect in the sensor panel, wherein the determination unit determines any defect in the sensor panel based on a signal value read after varying a potential difference between each signal line and the corresponding bias line or a signal value read after turning-on or turning-off of each switching element during a readout operation from the corresponding radiation detecting element.

According to another aspect of the present invention, there is provided a radiographic image capturing system, including: a radiographic image capturing apparatus including a sensor panel provided with scanning lines, signal lines, a two-dimensional array of radiation detecting elements each having a first electrode and a second electrode, bias lines each applying a reverse bias voltage to the corresponding radiation detecting element, and switching elements, the first electrode of each radiation detecting element being connected to the corresponding bias line, the second electrode of the radiation detecting element being connected to the corresponding signal line via the corresponding switch element; and a determination unit determining any defect in the sensor panel of the radiographic image capturing apparatus, wherein the determination unit determines any defect in the sensor panel of the radiographic image capturing apparatus based on a signal value read after varying a potential difference between each signal line and the corresponding bias line in the radiographic image capturing apparatus or a signal value read after turning-on or turning-off of each switching element during a readout operation from the corresponding radiation detecting element.

BRIEF DESCRIPTION OF THE DRAWINGS

The present invention will become more fully understood from the detailed description given hereinbelow and the appended drawings, and thus are not intended to define the limits of the present invention, and wherein.

DETAILED DESCRIPTION OF PREFERRED EMBODIMENTS

Embodiments of a radiographic image capturing apparatus and a radiographic image capturing system according to the present invention will now be described with reference to the accompanying drawings.

The radiographic image capturing apparatus described below is of an indirect type and includes a scintillator. The indirect type radiographic image capturing apparatus converts incident radiation into electromagnetic waves with a different wavelength, such as visible light, to obtain electric signals. Alternatively, the radiographic image capturing apparatus may be of a direct type, which detects radiation directly with detecting elements without using a scintillator.

The radiographic image capturing apparatus described below is a portable type. Alternatively, the radiographic image capturing apparatus may be a dedicated type, which is integrated with a holder.

[About Radiographic Image Capturing Apparatus]

Figure 1:
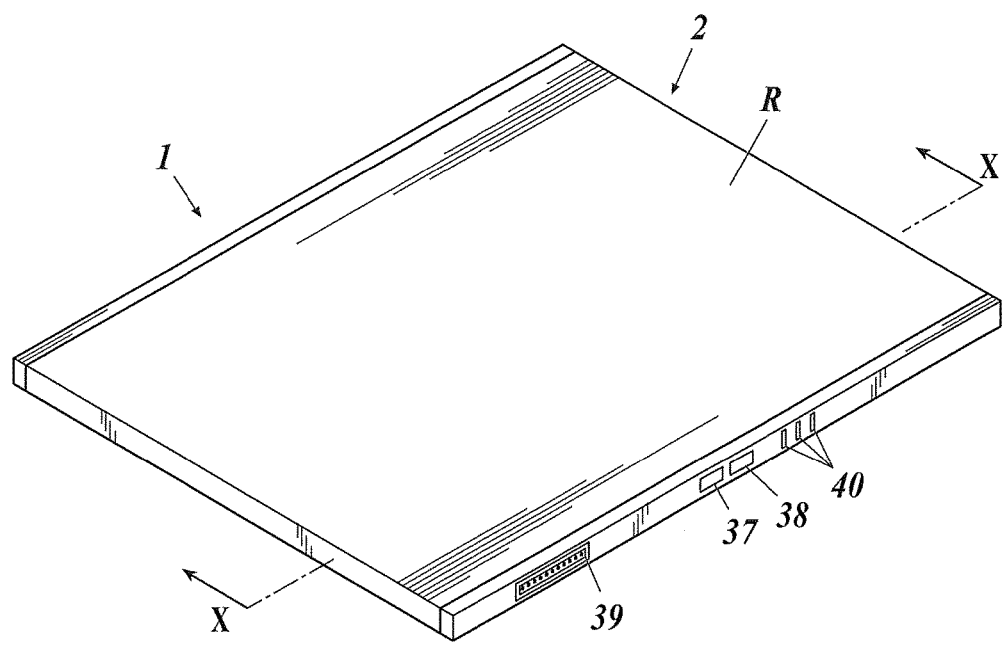
FIG. 1 is a perspective view of an outer appearance of a radiographic image capturing apparatus according to this embodiment.
Figure 2:
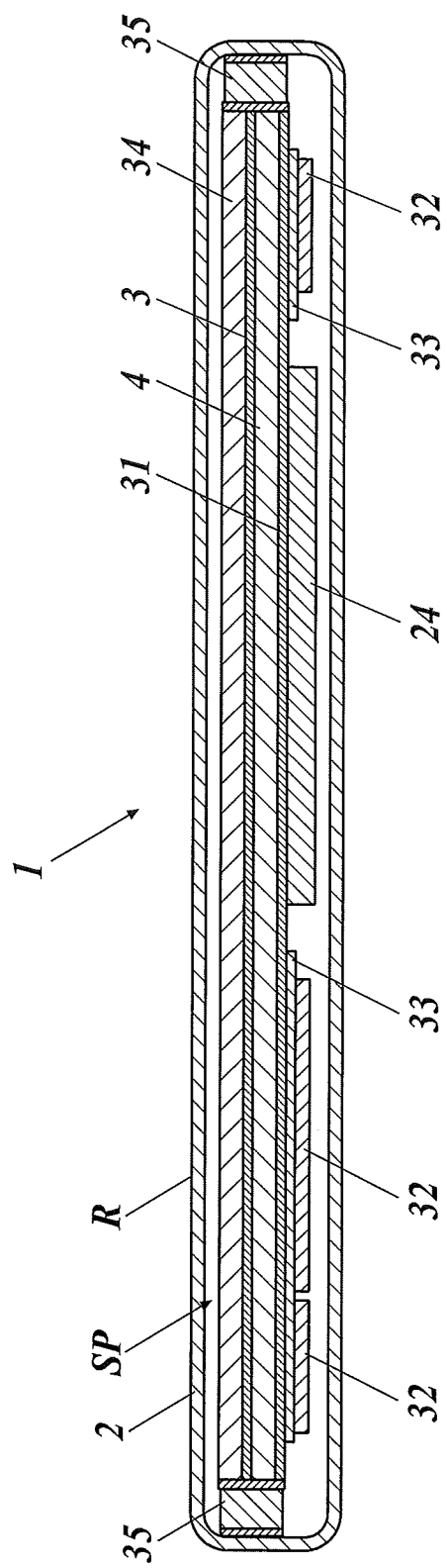
FIG. 2 is a cross sectional view along the line X-X in FIG. 1.

A configuration of the radiographic image capturing apparatus according to this embodiment will now be described. FIG. 1 is a perspective view of the outer appearance of the radiographic image capturing apparatus according to this embodiment. FIG. 2 is a cross sectional view cut along the line X-X in FIG. 1. For the vertical direction of the radiographic image capturing apparatus 1, the following description is based on the assumption that the radiographic image capturing apparatus 1 is disposed as shown in FIG. 2. In other words, the upper face of the radiographic image capturing apparatus 1 is a radiation incident surface R to which radiation enters.

With reference to FIG. 1, a housing 2 of the radiographic image capturing apparatus 1 has a power switch 37, a changing-over switch 38, a connector 39, an indicator 40, and any other component on one side face. The housing 2 further includes an antenna 41 (refer to FIG. 4 (described below)) for establishing wireless communication with an external device on the opposite side face (not shown).

With reference to FIG. 2, the housing 2 has a base 31 inside thereof. The base 31 is provided with a sensor board 4 thereon via a thin lead plate (not shown). The sensor board 4 is provided with the radiation detecting elements 7 thereon, which is described below. Above the sensor board 4, a scintillator board 34 is provided with a scintillator 3 thereon. The scintillator 3 and the scintillator board 34 are disposed such that the scintillator 3 faces the radiation detecting elements 7 disposed on the sensor board 4.

The base 31 is provided with a printed circuit board (PCB) 33 and a built-in power supply 24 on the bottom thereof. The PCB 33 is provided with an electronic component 32 thereon. These components in this embodiment together constitute a sensor panel SP. The sensor panel SP is provided with bumpers 35 at the lateral ends thereof, each bumper being disposed between one lateral end of the sensor panel SP and the corresponding side face of the housing 2.

Figure 3:
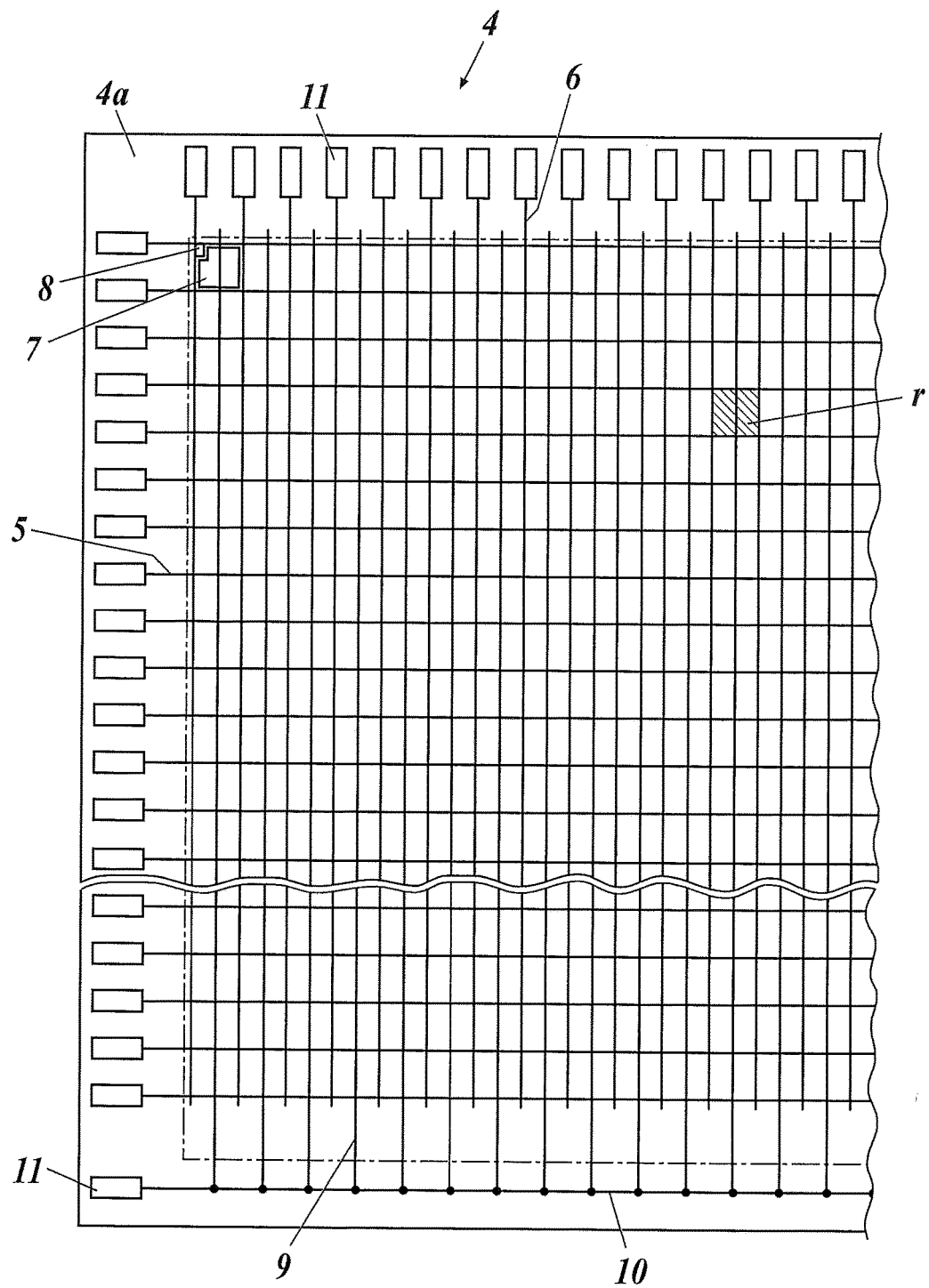
FIG. 3 is a plan view illustrating a configuration of a sensor board in the radiographic image capturing apparatus.

With reference to FIG. 3, the sensor board 4 is provided with multiple scanning lines 5 and multiple signal lines 6 on its upper face 4a, which faces the scintillator 3, such that the scanning lines 5 intersect with the signal lines 6. Regions r defined by the scanning lines 5 and the signal lines 6 are provided with radiation detecting elements 7. In this embodiment, the radiation detecting elements 7 are disposed in a two-dimensional array (matrix).

In this embodiment, multiple bias lines 9 extend parallel to the signal lines 6 and are connected to an interconnection 10. The sensor board 4 is provided with multiple I/O terminals 11 in the periphery thereof. The I/O terminals 11 are connected to the respective scanning line 5, the respective signal lines 6 or the interconnection 10. The I/O terminals 11 are connected to a flexible circuit board (not shown) having chips, such as a readout IC 16 (described below), disposed on a film. The flexible circuit board is connected to the PCB 33 at the rear face of the sensor board 4.

Figure 4:
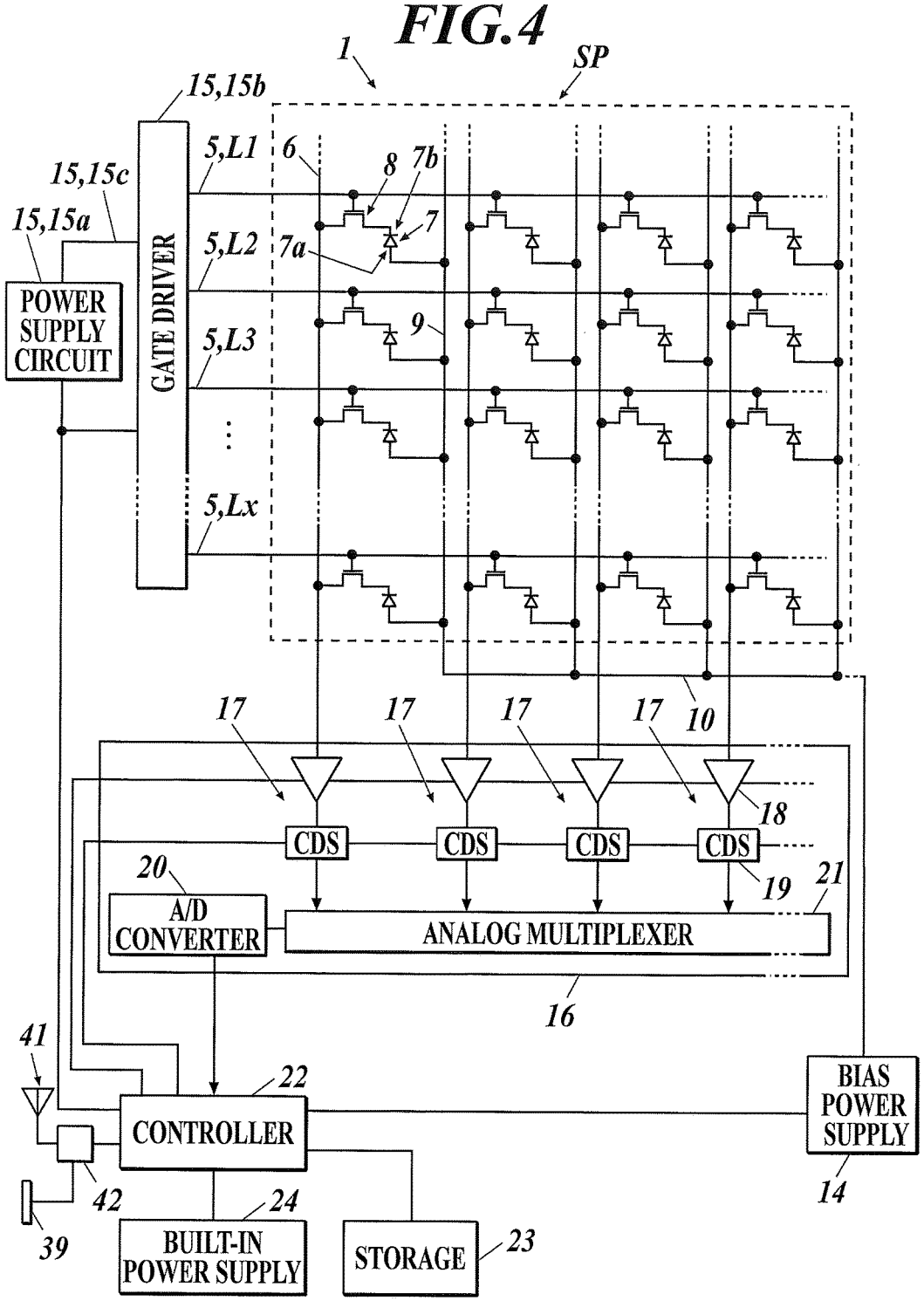
FIG. 4 is a block diagram illustrating an equivalent circuit of a radiographic image capturing apparatus.
Figure 5:
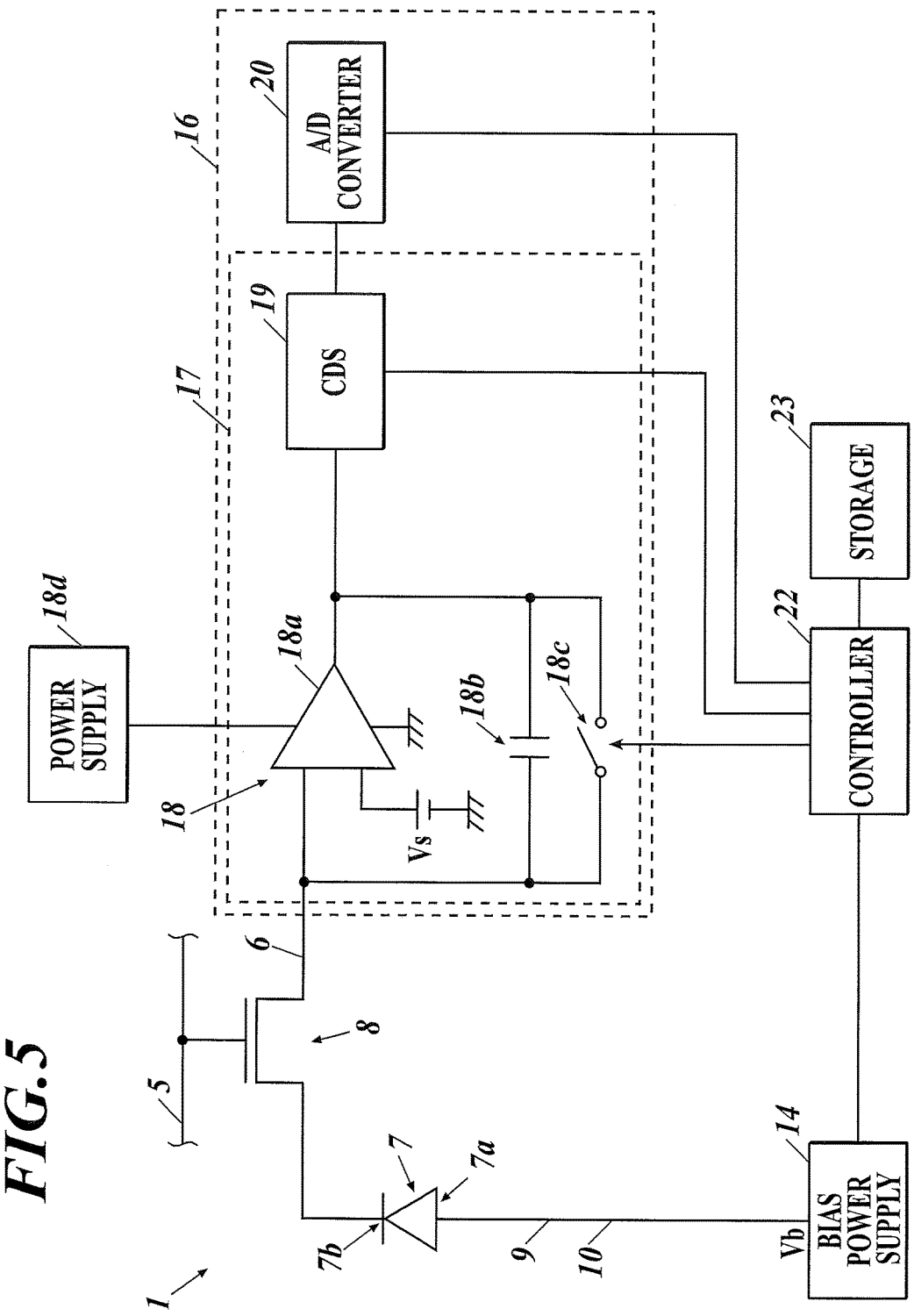
FIG. 5 is a block diagram illustrating an equivalent circuit of a single radiation detecting element.

A circuit configuration of the radiographic image capturing apparatus 1 will now be described. FIG. 4 is a block diagram illustrating an equivalent circuit of the radiographic image capturing apparatus 1. FIG. 5 is a block diagram illustrating an equivalent circuit of the single radiation detecting element 7, i.e., one pixel.

The radiation detecting elements 7 generate electric charges therein in proportion to the dose of radiation passing through a subject (not shown) or the light quantity of electromagnetic waves converted by the scintillator 3. In the following description, the radiation detecting elements 7 are photodiodes. Alternatively, the radiation detecting elements 7 may be photo-transistors or charge coupled devices (CCDs).

Each radiation detecting element 7 has an electrode 7a at one end. The electrodes 7a are connected to the respective bias lines 9. A bias power supply 14 applies a reverse bias voltage Vb via the bias lines 9 and the interconnection 10 to the radiation detecting elements 7. Each radiation detecting element 7 has an electrode 7b at the other end. The electrodes 7b are connected to the respective TFTs 8. The TFTs 8 function as switching elements and are connected to the respective signal lines 6.

An on-voltage applied to the TFTs 8 from a scan driving unit 15 (described below) via the scanning lines 5 puts the TFTs 8 into the on-state, resulting in release of electric charges accumulated in the radiation detecting elements 7 to the signal lines 6. In contrast, an off-voltage applied to the TFTs 8 via the scanning lines 5 puts the TFTs 8 into the off-state, resulting in a stop of release of electric charges from the radiation detecting elements 7 to the signal lines 6 and accumulation of electric charges in the radiation detecting elements 7.

The scanning lines 5 are connected to a gate driver 15b of the scan driving unit 15. The scan driving unit 15 applies an on-voltage or off-voltage from a power circuit 15a to the gate driver 15b via a line 15c. The gate driver 15b can switch a voltage applied to the scanning lines 5(L1) to 5(Lx) between on-voltage and off-voltage.

The signal lines 6 are connected to respective readout circuits 17 in the readout IC 16. Each readout circuit 17 in this embodiment includes an integrating circuit (charge amplifier) 18 and a correlated double sampling circuit 19. The readout IC 16 further includes an analog multiplexer 21 and an A/D converter 20. In FIGS. 4 and 5, the correlated double sampling circuits 19 are indicated as "CDS".

Each integrating circuit 18 in this embodiment includes an operational amplifier 18a having an inverted input terminal and an output terminal, a capacitor 18b disposed between the inverted input terminal and the output terminal, an electric charge resetting switch 18c to release electric charge accumulated in the capacitor 18b, and a power supply 18d to supply power to the operational amplifier 18a. The inverted input terminal of the operational amplifier 18a in each integrating circuit 18 is connected to the signal line 6. A reference potential is applied to the inverted input terminal of the operational amplifier 18a.

Since the reference potential is applied to each signal line 6 via the corresponding operational amplifier 18a, the reference potential is referred to as a "signal line voltage Vs". The electric charge resetting switch 18c in the integrating circuit 18 is turned on or off by a controller 22.

Upon emission of radiation from the radiation emitting apparatus (not shown) to the radiographic image capturing apparatus 1 in a capturing mode while the TFTs (switching elements) are in the off-state, electric charges generated in the radiation detecting elements 7 are accumulated in the radiation detecting elements 7.

During reading of image data D from each radiation detecting element 7, the electric charge resetting switch 18c in the integrating circuit 18 is turned off, putting the integrating circuit 18 into the integral state. The correlated double sampling circuit 19 then performs the first sample-and-hold operation. In the sample-and-hold state, an on-voltage is applied to the TFT 8 connected to the radiation detecting element 7 to be read, resulting in release of electric charge from the radiation detecting element 7 to the signal line 6.

The released electric charge flows into the capacitor 18b of the integrating circuit 18 in each readout circuit 17 and is accumulated in the capacitor 18b. The operational amplifier 18a outputs a voltage value in proportion to the electric charge accumulated in the capacitor 18b. The integrating circuit 18 outputs a voltage value before the application of an on-voltage to the TFT 8 connected to the radiation detecting element 7 to be read. After the application of an on-voltage, electric charge is released from the radiation detecting element 7 and then an off-voltage is applied to the TFT 8. At this timing, the integrating circuit 18 outputs a voltage value. The correlated double sampling circuit 19 then calculates and outputs a difference (increase) between the pre-application voltage value and the post-application voltage value output from the integrating circuit 18 in the form of analog image data D.

The image data D output from the correlated double sampling circuit 19 is sequentially transmitted through an analog multiplexer 21 to an A/D converter 20, converted into digital image data D at the A/D converter 20, and stored in a storage 23. This operation is repeated at each scanning operation and image data D is thereby read.

The controller 22 includes a central processing unit (CPU), a read-only memory (ROM), a random-access memory (RAM), a computer having a bus connected to, for example, an input-output interface, a field programmable gate array (FPGA), and any other components that are not shown in the drawings. The controller 22 may be a dedicated controlling circuit.

The controller 22 is connected to the storage 23, which may be a static RAM (SRAM), a synchronous DRAM (SDRAM), or a NAND flash memory, and a built-in power supply 24, which may be a lithium ion capacitor. The controller 22 is also connected to a communication unit 42 for communicating with an external device through a wireless or wired network via the antenna 41 or the connector 39.

The controller 22 controls the application of a reverse bias voltage Vb from the bias power supply 14 to the radiation detecting elements 7 and the operations of the scan driving unit 15 and the readout circuits 17 as described above, so that the image data D is read from the radiation detecting elements 7 and stored in the storage 23. The controller 22 also controls the transfer of the image data D stored in the storage 23 to an external device via the communication unit 42.

First Embodiment

The radiographic image capturing apparatus 1 according to the first embodiment of the present invention will now be described. The radiographic image capturing apparatus 1 according to this embodiment includes a determination unit that determines any defect in the sensor panel SP. The determination unit determines any defect in the sensor panel SP based on signal values S read after varying a potential difference ΔV between each signal line 6 and the corresponding bias line 9.

Figure 6:
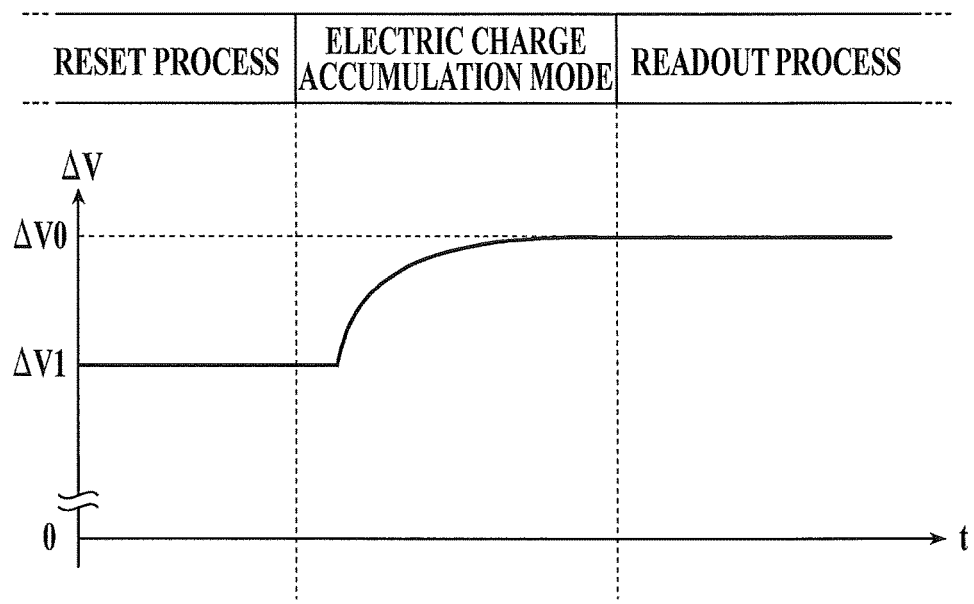
FIG. 6 is a graphical representation of a potential difference between the electrodes of a radiation detecting element during processes and in a state in a determination process.

With reference to FIG. 6, the determination process consists of reset, accumulation, and readout processes. The reset process to reset the radiation detecting elements 7 applies an on-voltage to gate electrodes (the scanning lines 5) of the TFTs 8, while a potential difference between the signal line voltage Vs and the reverse bias voltage Vb is set to a predetermined potential difference ΔV1, to apply an initial potential difference ΔV1 between the two electrodes 7a and 7b of each radiation detecting element 7 (see FIG. 4 and FIG. 5). The reset process thus provides the radiation detecting elements 7 with an initial electric charge.

The accumulation process (electric charge accumulation mode) applies an off-voltage to the gate electrodes of the TFTs 8 (the scanning lines 5) to retain electric charges in the radiation detecting elements 7. When radiation is emitted, the initial electric charge is reduced by electric charge in proportion to the dose of emitted radiation. For simplicity, this process is referred to as "accumulation of electric charge".

The readout process (of signal values S) applies an on-voltage to the gate electrodes of TFTs 8 (the scanning lines 5), while the potential difference between the signal line voltage Vs and the reverse bias voltage Vb is set to a predetermined potential difference ΔV0, to apply a potential difference ΔV0 between the two electrodes 7a and 7b of each radiation detecting element 7. The application of the potential difference results in transfer of electric charge. The transferred electric charge is read to obtain signal values S.

In the following description, the determination process is explained in detail. The controller 22 of the radiographic image capturing apparatus 1 according to this embodiment functions as the determination unit. The controller 22 is hereinafter referred to as the "determination unit 22". Alternatively, the determination unit 22 may be separated from the controller 22.

Figure 7:
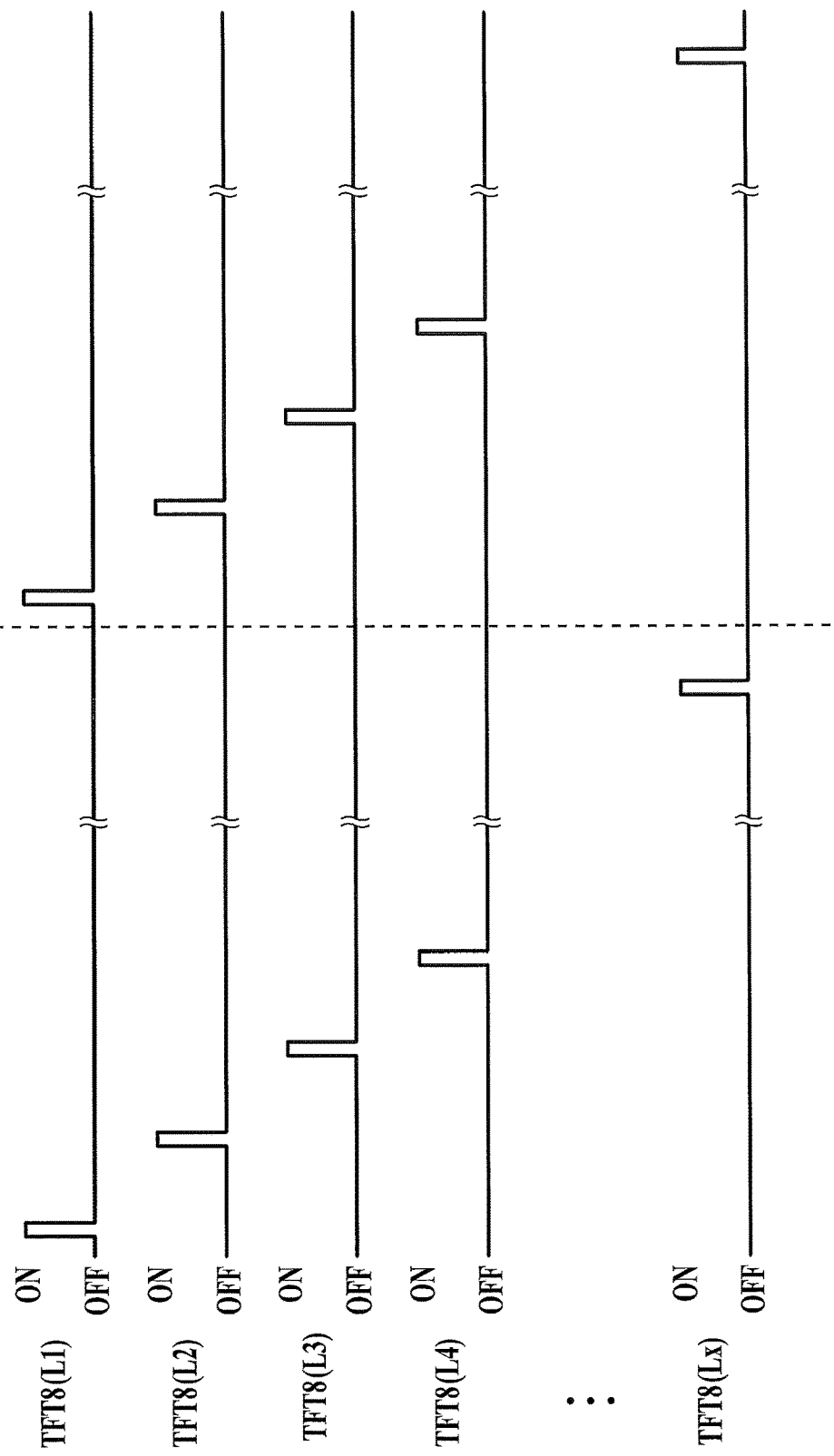
FIG. 7 is a timing chart illustrating timing for sequentially applying an on-voltage to the TFTs during sequential application of an on-voltage to the scanning lines to reset the radiation detecting elements.

With reference to FIG. 7, the determination unit 22 resets the radiation detecting elements 7 as follows: The determination unit 22 sequentially applies an on-voltage from the gate driver 15b of the scan driving unit (see FIG. 4) to the scanning lines 5(L1) to 5(Lx) to sequentially put the TFTs 8 into the on-state. This operation releases electric charges from the radiation detecting elements 7 to the signal lines 6 to remove electric charges remaining in the radiation detecting elements 7.

Alternatively, the radiation detecting elements 7 may be reset by concurrently applying an on-voltage to the scanning lines 5(L1) to 5(Lx), instead of sequentially applying an on-voltage to the scanning lines 5(L1) to 5(Lx). In the following description, the reset process of the radiation detecting elements 7 will be described in detail. Since the purpose of the reset process is to remove electric charges remaining in the radiation detecting elements 7, the readout process, for example, may be performed to read image data D from the radiation detecting elements 7, as described above, instead of performing the reset process of the radiation detecting elements 7.

If the potential difference ΔV0 between each signal line 6 and the corresponding bias line 9 for reading image data D from the radiation detecting elements 7 during a normal capture is, for example, 5[V], the determination unit 22 sets the potential difference ΔV1 between each signal line 6 and the corresponding bias line 9 for performing the reset process of the radiation detecting elements 7 to an absolute value smaller than the potential difference ΔV0, for example, 4.5[V], as shown in FIG. 6, to reset the radiation detecting elements 7.

As described above, the reverse bias voltage Vb is applied to the electrode 7a, at one end, of each radiation detecting element 7, while the signal line voltage Vs is applied to the signal line 6 connected to the electrode 7b, at the other end, of the radiation detecting element 7 via the corresponding TFT 8. The potential difference ΔV between each signal line 6 and the corresponding bias line 9 is calculated as follows:

$$\Delta V = Vs - Vb \quad (1)$$

The connection of the electrode 7b, at the other end, of each radiation detecting element 7 to the corresponding signal line 6 via the corresponding TFT 8 is simply referred to as "connection of the electrode 7b, at the other end, of each radiation detecting element 7 to the signal line 6".

In this embodiment, if either or both of the reverse bias voltage Vb and the signal line voltage Vs is/are varied during the reset process or during the readout process, a post-reset or post-readout potential difference ΔV between each signal line 6 and the corresponding bias line 9 can be varied during the reset process or during the readout process. The signal line voltage Vs can be varied by varying a reference potential applied to the inverted input terminal of the operational amplifier 18a (see FIG. 5) of the integrating circuit 18 in the readout circuit 17.

The reverse bias voltage Vb may be varied by, for example, varying the resistance of a voltage divider of a voltage value output from the bias power supply 14. This technique is also applicable to the signal line voltage Vs. Alternatively, at least two bias supplies 14 that output different reverse bias voltages Vb are provided to switch between them. Any other technique may be used for varying the reverse bias voltage Vb and/or the signal line voltage Vs.

With reference to FIG. 6, the determination unit 22 resets the radiation detecting elements 7, while the potential difference between each signal line 6 and the corresponding bias line 9 sets to ΔV1 (for example, 4.5[V]), to set the potential difference between the two electrodes 7a and 7b of each radiation detecting element 7 to ΔV1. The determination unit 22 instructs the gate driver 15b to apply an off-voltage to the scanning lines 5(L1) to 5(Lx) to put the TFTs 8 into the off-state. This results in transition to the electric charge accumulation mode involving accumulation of electric charges in the radiation detecting elements 7. In the electric charge accumulation mode, radiation would be emitted if a diagnostic image is to be captured. However, for the purpose of fault diagnosis according to the present invention, the following process is performed, instead of emitting radiation.

In the electric charge accumulation mode, the reverse bias voltage Vb and/or the signal line voltage Vs is/are varied until the potential difference ΔV0 is achieved and then the readout process is performed. Since the reverse bias voltage Vb and the signal line voltage Vs vary according to a given time constant, the readout process should start after the variation in potential difference is stabilized. In general, a time to wait for the start of the readout process should preferably at least equal six times the time constant.

As described above, putting the TFTs into the on-state during the readout process sets the potential difference between the two electrodes 7a and 7b of each radiation detecting element 7 to ΔV0. The readout process reads electric charge Q=(ΔV0−ΔV1)×C (Capacitance (C) of each radiation detecting element 7) to obtain a signal value S.

The determination of any defect in the sensor panel SP by the determination unit 22 is described later.

[Operations]

The operations of the radiographic image capturing apparatus according to this embodiment 1 will now be described. In the above configuration, the potential difference between the two electrodes 7a and 7b of each radiation detecting element 7 is retained at $\Delta V1$ (for example, 4.5[V]) in the electric charge accumulation mode, as shown in FIG. 6. The readout process reads electric charge that sets the potential difference between the two electrodes of each radiation detecting element 7 to $\Delta V0$ and then sets the potential difference to $\Delta V0$ (for example, 5[V]). During the readout process, electric charge $Q=C\times(\Delta V0-\Delta V1)$ is read to output a signal value S.

In this embodiment, the electric charge Q can be generated in each radiation detecting element 7 by varying the potential difference $\Delta V$ between each signal line 6 and the corresponding bias line 9 from $\Delta V1$ at the time of reset to $\Delta V0$ during the readout process, as described above. This allows the same state as emission of radiation to the radiographic image capturing apparatus 1 in a capturing mode to be created even if the radiographic image capturing apparatus 1 is not exposed to radiation.

In other words, creation of the same state as that of this embodiment does not necessarily require variation in the potential difference $\Delta V$ between each signal line 6 and the corresponding bias line 9 from $\Delta V1$ to $\Delta V0$, just as in this embodiment. Just emission of radiation from the radiation emitting apparatus to the radiographic image capturing apparatus 1 without a subject can accumulate electric charge generated in the radiation detecting elements 7 into the radiation detecting elements 7.

Unfortunately, radiation is not always emitted evenly to the radiation incident surface R (refer to FIG. 1) of the radiographic image capturing apparatus 1, which results in unevenness in radiation intensity. In general, generating a uniform quantity (Q) of electric charge in the radiation detecting elements 7 is difficult when radiation is emitted to the radiographic image capturing apparatus 1. Moreover, adjusting the radiation of X-rays requires a lot of work and causes burdensome radiation of X-rays.

In contrast, the radiographic image capturing apparatus 1 according to this embodiment can generate electric charge (Q) corresponding to a variation in the potential difference $\Delta V$ ($\Delta V0-\Delta V1$) between each signal line 6 and the corresponding bias line 9 accumulate the charge in each radiation detecting element 7. Accordingly, the radiographic image capturing apparatus 1 according to this embodiment can determine any defect in the sensor panel SP more accurately than the determination based on image data D obtained by emitting radiation to the radiographic image capturing apparatus 1.

The radiographic image capturing apparatus 1 according to this embodiment can obtain signal values S, which are comparable with or superior to the image data D obtained by emitting radiation, without emission of radiation. This eliminates the necessity for a radiological technician to emit radiation from the radiation emitting apparatus in order to determine any defect in the sensor panel SP, thus saving the effort involved in the above determination process. The determination unit 22, which can perform determination process without emission of radiation, can be performed any time, which advantageous effects will be described below.

As described above, the method disclosed in Japanese Unexamined Patent Application Publication No. 2011-67334 neither involves emission of radiation to the radiographic image capturing apparatus 1 nor variation in the potential difference $\Delta V$ between each signal line 6 and the corresponding bias line 9 (kept at $\Delta V0$ in the above example). In this case, dark electric charges are accumulated in the radiation detecting elements 7 and the signal values obtained by reading the dark electric charges (the pixel values of the offset image in Japanese Unexamined Patent Application Publication No. 2011-67334) are several orders of magnitude smaller than the image data D read after, for example, emitting radiation to the radiographic image capturing apparatus 1.

The analysis of the offset image does not lead to an accurate detection of any disconnection in the signal lines 6 or the bias lines 9. Detection of any disconnection in the scanning lines 5 is also difficult by this method.

In contrast, the radiographic image capturing apparatus 1 according to this embodiment varies the potential difference $\Delta V$ between each signal line 6 and the corresponding bias line 9, accumulates electric charge Q equivalent to the variation in potential difference $\Delta V$ ($\Delta V0-\Delta V1$) in each radiation detecting element 7, and reads signal values S. The signal values S can be increased to the magnitude of the image data D read after emitting radiation to the radiographic image capturing apparatus 1 by adjusting the amount of variation ($\Delta V0-\Delta V1$). In other words, the signal values S read by the radiographic image capturing apparatus 1 according to this embodiment can increase to a value which is several orders of magnitude larger than the pixel values of the offset image read by the method disclosed in Japanese Unexamined Patent Application Publication No. 2011-67334.

In the case of disconnection in, for example, the signal lines 6, electric charge Q cannot be read from radiation detecting elements 7, connected to the broken signal line 6, away from the broken point in the direction remote from the readout IC. A signal value S read from such a radiation detecting element 7 is significantly lower than that corresponds to electric charge Q. This allows the radiographic image capturing apparatus 1 according to this embodiment to detect any disconnection in the signal lines 6 properly and efficiently based on the signal values S and determine any signal line disconnection from a linear defect (also referred to as a "line defect").

In the case of any disconnection in the bias lines 9, electric charge Q cannot be obtained due to an inability to apply a bias voltage to the radiation detecting elements 7. For comb-shaped bias lines, any disconnection in the bias lines is detected as a linear defect, just as the disconnection of any signal line, allowing the operator to determine a disconnection in either the signal lines or the bias lines. For reticular bias lines, no abnormal signal value is obtained from normally connected radiation detecting elements 7 or any disconnection of a bias line in a pixel section is detected as a single pixel error, depending on the location of the disconnection. A bias line disconnection may be distinguished from a signal line disconnection, depending on design of the TFT lines.

Figure 8:
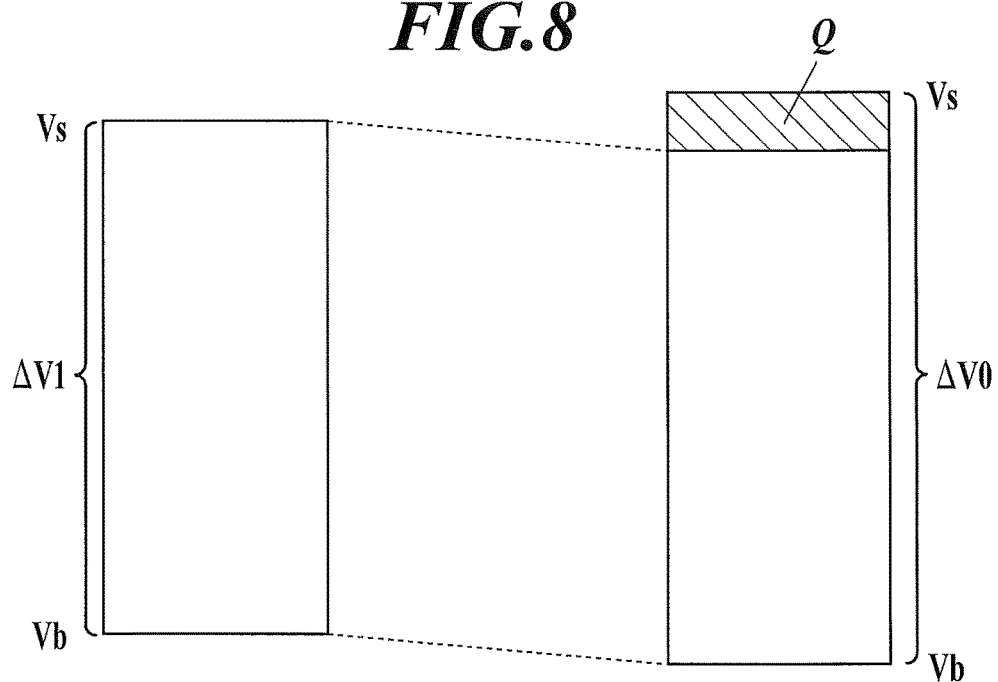
FIG. 8 illustrates the accumulation of electric charge in each radiation detecting element in response to variations in a potential difference between the electrodes of the radiation detecting element in an electric charge accumulation mode.

If the radiographic image capturing apparatus 1 is configured such that the reverse bias voltage Vb, for example, is varied to vary the potential difference $\Delta V$ between each signal line 6 and the corresponding bias line 9, the radiation detecting elements 7 connected to the broken bias line 9 do not undergo a variation in the potential difference $\Delta V$ since the reverse bias voltage Vb is constant and do not generate electric charge Q as shown in FIG. 8.

If the radiographic image capturing apparatus 1 is configured such that the signal line voltage Vs, for example, is varied to vary the potential difference ΔV between each signal line 6 and the corresponding bias line 9, a broken bias line 9 also results in no generation of electric charge Q, as shown in FIG. 8. This is because when the signal line voltage Vs is varied to vary the potential difference at the electrode 7b of each radiation detecting element 7, the potential at the electrode 7a of the radiation detecting element 7 is also varied.

In either case, the signal values S read from the radiation detecting elements 7 are equivalent to those generated from the dark electric charges in Japanese Unexamined Patent Application Publication No. 2011-67334 and an order of magnitude smaller than the signal values S read from the radiation detecting elements 7 connected to normally connected bias lines 9. Thus, the radiographic image capturing apparatus 1 according to this embodiment allows a broken bias line 9 to be detected properly and efficiently based on the signal values S.

If a scanning line 5 is disconnected, the TFTs 8 cannot be turned on or off and electric charge Q from pixels remote from the gate driver 15b cannot be read, resulting in a linear defect. Thus, the radiographic image capturing apparatus 1 according to this embodiment allows a broken scanning line 5 to be detected properly and efficiently based on the signal values S.

Advantageous Effects

As described above, the determination unit 22 in the radiographic image capturing apparatus 1 according to this embodiment determines any defect in the sensor panel SP based on the signal values S read after varying the potential difference ΔV between each signal line 6 and the corresponding bias line 9.

This allows the radiographic image capturing apparatus 1 to detect any disconnection in lines, such as the scanning lines 5, the signal lines 6 or the bias lines 9, in the radiographic image capturing apparatus 1 properly and accurately and determine any defect in the sensor panel SP properly and accurately.

Second Embodiment

The radiographic image capturing apparatus 1 according to the second embodiment of the present invention will now be described. The radiographic image capturing apparatus 1 according to the first embodiment varies the potential difference ΔV between each signal line 6 and the corresponding bias line 9 to generate electric charge Q, reads the electric charge Q in the form of signal values S, and determines any defect in the sensor panel SP in the radiographic image capturing apparatus 1 based on the read signal values S.

The radiographic image capturing apparatus 1 having, for example, any of the following configurations does not vary the potential difference ΔV between each signal line 6 and the corresponding bias line 9 to generate electric charge Q, but can read the signal values without emission of radiation to the radiographic image capturing apparatus 1 and determine any defect in the sensor panel SP based on the read signal values.

[Configuration 1]

The determination unit 22 according to this embodiment can be configured to turn on the TFTs 8 (switching elements) before a correlated double sampling operation reading signal values S from the radiation detecting elements 7, to turn off the TFTs 8 during the correlated double sampling operation reading signal values S*, and then to determine any defect in the sensor panel SP based on the read signal values S*.

[Configuration 2]

Alternatively, the determination unit 22 can be configured to turn on the TFTs 8 during a correlated double sampling operation, to turn off the TFTs 8 after the correlated double sampling operation reading signal values S, and then to determine any defect in the sensor panel SP based on the read signal values S.

In the above description, the configurations involving a correlated double sampling operation are used. Alternatively, a configuration that does not involve the correlated double sampling operation may be used. For example, the determination unit turns on the TFTs 8 during an electric charge reset operation of the integrating circuit, turns off the TFTs 8 during an integration operation with the electric charge reset operation of the integrating circuit disabled, performs sampling in this state, and performs an analog-to-digital conversion to read signal values S*.

Alternatively, the analog-to-digital conversion may be performed directly without sampling. Alternatively, the determination unit turns on the TFTs 8 during an integration operation, performs sampling in this state, and performs an analog-to-digital conversion to read signal values S. In this case, the TFT 8** is turned off, for example, after the sampling or the analog-to-digital conversion.

Before description of the configurations 1 and 2, switching timing of signals sent from the controller 22 to the readout circuit 17 (see FIG. 4 or 5) and outputs from the integrating circuit 18 during the readout process of image data D will now be described with reference to FIG. 9.

Figure 9:
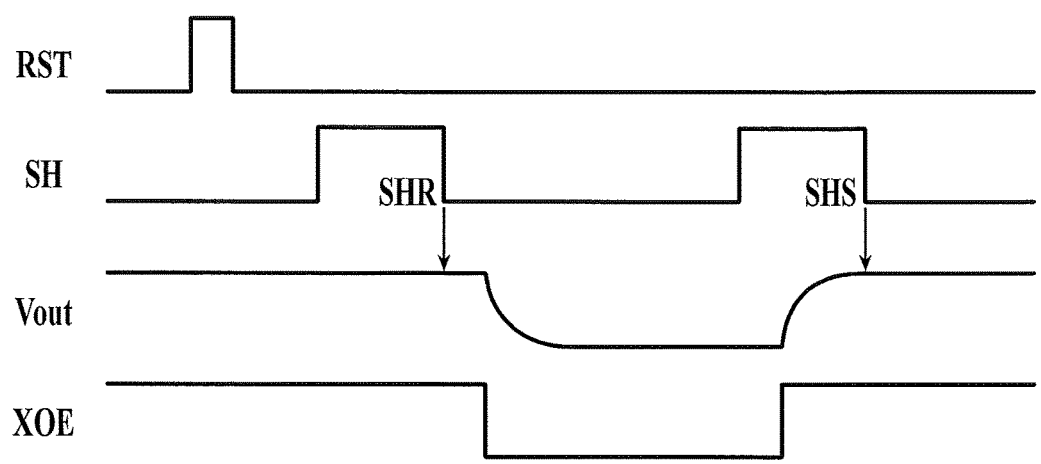
FIG. 9 illustrates timing for sending pulse signals in a readout process of image data and a temporal change in voltage values output from an operational amplifier.
Figure 10:
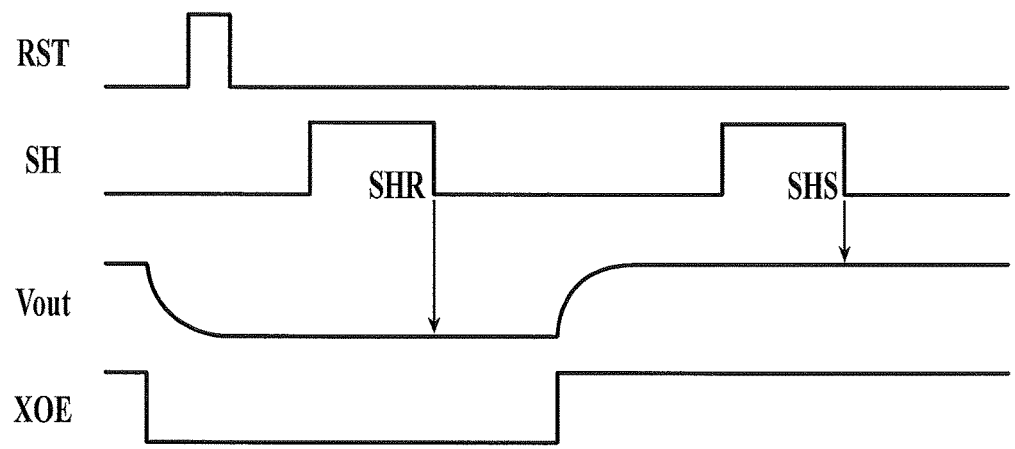
FIG. 10 illustrates timing for sending pulse signals and a temporal change in voltage values output from the operational amplifier in exemplary Configuration 1.
Figure 11:
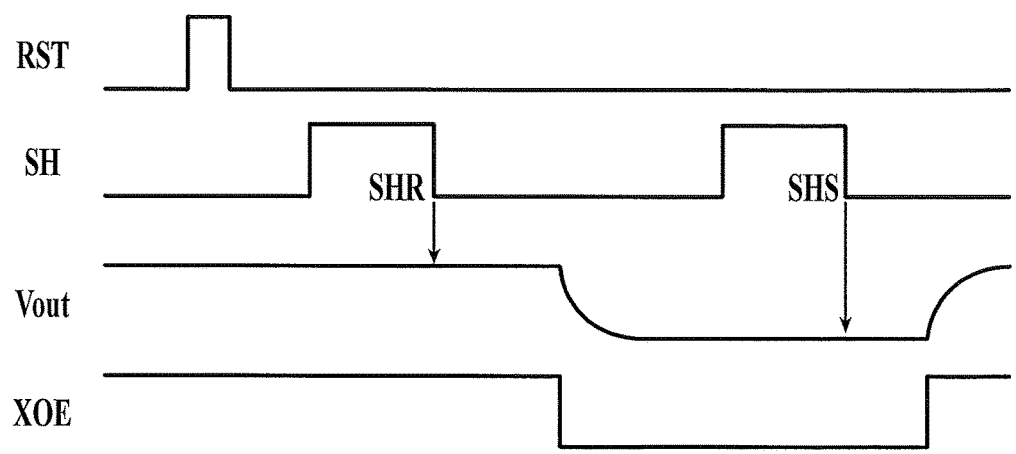
FIG. 11 illustrates the timing for sending pulse signals and a temporal change in voltage values output from the operational amplifier in exemplary configuration 2.

FIGS. 9 to 11 illustrate a cycle of turning on and off a single TFT 8. In FIGS. 9 to 11, RST represents a pulse signal to reset each readout circuit 17 in the readout IC 16. SH represents a pulse signal to perform a sample-and-hold operation at the correlated double sampling circuit 19 (SHR and SHS represent a pulse signal for the first and second sample-and-hold operations, respectively). In this embodiment, the sample-and-hold operation is performed at the falling edge of SH (SHR and SHS).

In FIGS. 9 to 11, Vout represents a voltage value output from the operational amplifier 18a of the readout circuit 17. XOE represents an off-voltage or on-voltage applied to the TFT 8 (H and L represent an off-voltage and an on-voltage, respectively).

In the readout process of image data D (or dark image o (described below)), the reset process is performed at each readout circuit 17 based on a pulse signal (RST) sent from the controller 22, as shown in FIG. 9. Upon receipt of a first pulse signal (SHR) that directs a sample-and-hold operation from the controller 22, the correlated double sampling circuit 19 samples and holds a voltage value Vout output from the operational amplifier 18a (the voltage value Vout at this timing is referred to as "Vout1") at the falling edge of SHR.

The controller 22 applies an on-voltage to the TFT 8 from the gate driver 15b through the scanning line 5 to turn on the TFT 8 (XOE: H→L). This operation temporarily reduces the voltage value Vout output from the operational amplifier 18a. The controller 22 then applies an off-voltage to the TFT 8 from the gate driver 15b through the scanning line 5 to turn off the TFT 8 (XOE: L→H). This operation raises the voltage value Vout output from the operational amplifier 18a again. Upon receipt of a second pulse signal (SHS) that directs a sample-and-hold operation from the controller 22, the correlated double sampling circuit 19 samples and holds a voltage value Vout output from the operational amplifier 18a (the voltage value Vout at this timing is referred to as "Vout2") at the falling edge of SHS.

If the radiation detecting elements 7 have electric charge generated, just like in a capturing mode, through emission of radiation to the radiographic image capturing apparatus 1 before the readout process, as shown in FIG. 9, the voltage values Vout1 and Vout2 sampled and held by the correlated double sampling circuit 19 have a significant difference, which is read in the form of image data D, as described above. In contrast, if no radiation is emitted to the radiographic image capturing apparatus 1, just like the readout process of the dark image o (described below), the voltage values Vout1 and Vout2 have no significant difference and a difference between Vout2 and Vout1 is almost zero.

This is the end of the description on control of the readout process of the image data D (or the dark image o (described below)) in a capturing mode.

[Configuration 1]

FIG. 10 shows the readout process of a signal value S* in the determination process of Configuration 1 according to this embodiment. In the readout process, the determination unit 22 is configured to turn on and off the TFT 8 earlier than the on and off timing shown in FIG. 9. Unlike the first embodiment, this embodiment and Configuration 2 described below do not vary the potential difference ΔV between each signal line 6 and the corresponding bias line 9.

In the readout process of a signal value S* the determination process, the determination unit 22 applies an on-voltage to the TFT 8 from the gate driver 15b through the scanning line 5 to turn on the TFT 8 (XOE: H→L), as shown in FIG. 10. This operation temporarily reduces the voltage value Vout output from the operational amplifier 18a, as described above.

The determination unit 22 then sends a pulse signal (RST) to reset the readout circuit 17, sends a first pulse signal (SHR) to the correlated double sampling circuit 19, and samples and holds a voltage value Vout1 output from the operational amplifier 18a. The determination unit 22 then applies an off-voltage to the TFT 8 from the gate driver 15b through the scanning line 5 to turn off the TFT 8 (XOE: L→H). This operation raises the voltage value Vout output from the operational amplifier 18a again. The determination unit 22 sends a second pulse signal (SHS) to the correlated double sampling circuit 19 and samples and holds a voltage value Vout2 output from the operational amplifier 18a (Configuration 1).

This configuration results in a significant difference of Vout2−Vout1 between the voltage values Vout1 and Vout2 sampled and held by the correlated double sampling circuit 19, producing a signal value S* significantly different from zero. Although no radiation is emitted to the radiographic image capturing apparatus 1 in Configuration 1, the read signal value S* has a large value substantially equally large as the value of the image data D read from the radiographic image capturing apparatus 1 while radiation is emitted thereto, unlike the dark image o (with a magnitude of almost zero) read from the radiographic image capturing apparatus 1 while no radiation is emitted thereto.

The determination process according to the first embodiment determines any defect in the sensor panel SP of the radiographic image capturing apparatus 1 based on the signal values S read after varying a potential difference ΔV between each signal line 6 and the corresponding bias line 9. Unlike the first embodiment, the determination process of Configuration 1 turns on the TFTs 8 (switching elements) before a correlated double sampling operation to read signal values S from the radiation detecting elements 7, turns off the TFTs 8 during the correlated double sampling operation to read signal values S*, and determines any defect in the sensor panel SP based on the read signal values S*. The determination process of Configuration 1 can provide the same advantageous effects as the first embodiment.

[Configuration 2]

FIG. 11 shows the readout process of a signal value S** in the determination process of Configuration 2 according to this embodiment. The determination unit 22 sends a pulse signal (RST) to instruct the readout circuit 17 to perform the reset process and then sends a first pulse signal (SHR) to the correlated double sampling circuit 19 to instruct the correlated double sampling circuit 19 to sample and hold a voltage value Vout1 output from the operational amplifier 18a. The determination unit 22 then applies an on-voltage to the TFT 8 from the gate driver 15b through the scanning line 5 to turn on the TFT 8 (XOE: H→L). This operation temporarily reduces the voltage value Vout output from the operational amplifier 18a, as described above.

The determination unit 22 then sends a second pulse signal (SHS) to the correlated double sampling circuit 19 to instruct the correlated double sampling circuit 19 to sample and hold a voltage value Vout2 output from the operational amplifier 18a and then applies an off-voltage to the TFT 8 from the gate driver 15b through the scanning line 5 to turn off the TFT 8 (XOE: L→H) (Configuration 2). This operation raises the voltage value Vout output from the operational amplifier 18a again.

This configuration results in a significant difference of Vout2−Vout1 (a negative value in this case) between the voltage values Vout1 and Vout2 sampled and held by the correlated double sampling circuit 19, producing a signal value S significantly larger than zero. Although no radiation is emitted to the radiographic image capturing apparatus 1 in Configuration 2, the read signal value S (a negative value, unlike Configuration 1) has an absolute value substantially equally large as the value of the image data D read from the radiographic image capturing apparatus 1 while radiation is emitted thereto, unlike the dark image o (with a magnitude of almost zero) read from the radiographic image capturing apparatus 1 while no radiation is emitted thereto, similar to Configuration 1.

The determination process according to the first embodiment determines any defect in the sensor panel SP of the radiographic image capturing apparatus 1 based on the signal values S read after varying a potential difference ΔV between each signal line 6 and the corresponding bias line 9. Unlike the first embodiment, in the determination process of Configuration 2, the determination unit 22 turns on the TFTs 8 during the correlated double sampling operation, turns off the TFTs 8 after the correlated double sampling operation, reads signal values S and then determines any defect in the sensor panel SP based on the read signal values S. The determination process of Configuration 2 can provide the same advantageous effects as the first embodiment and Configuration 1.

When each TFT 8 is switched from off to on, a difference between the off-voltage and the on-voltage of the TFT 8 is input to the readout IC 16 to generate an electric charge signal due to a stray capacity between each scanning line and the corresponding signal line (for example, a stray capacity between the gate electrode and source electrode of each TFT 8). The input electric charge signal generates a signal value S. Similarly, when the TFTs 8 are switched from on to off, signal values S are also generated. Since the electric charge signals are transmitted through the scanning lines 5 and the signal lines 6, the above phenomenon allows any disconnection in the signal lines 5 or the signal lines 6 to be determined. A combination with the first embodiment can determine which line, signal line 6 or bias line 9, is broken, although the first embodiment alone cannot, depending on the design of the bias lines on the sensor panel SP.

[Configuration 3]

The determination process of Configuration 3 sends SHR to the correlated double sampling circuit 19, turns on the TFTs 8, varies the potential difference ΔV between each signal line and the corresponding bias line, turns off the TFTs 8, and sends SHS to the correlated double sampling circuit 19. The determination process of Configuration 3 can provide the same advantageous effects as Configuration 1.

[Determination of any Defect in the Sensor Panel SP]

Determination of any defect in the sensor panel SP in the determination unit 22 will now be described.

It is preferred to analyze an image obtained by subtracting the value of a reference dark image from the value of an image to be inspected (referred to as "offset correction") for improved accuracy. The dark image may be obtained without any variation in the potential difference between each signal line voltage and the corresponding bias line voltage in the electric charge accumulation state or at factory shipping. Alternatively, the dark image may be obtained by varying the potential difference between each signal line voltage and the corresponding bias line voltage in a reverse direction in the electric charge accumulation state.

In the following description, the first embodiment is taken as an example, although the same is applicable to the second embodiment. The determination unit 22 determines a reference signal value Sst that corresponds to the variation (ΔV0−ΔV1) in the potential difference ΔV between each signal line 6 and the corresponding bias line 9 (or the electric charge Q that corresponds to the variation). If a signal value S read from each radiation detecting element 7 is outside of a predetermined range around the reference signal values Sst (for example, Sst−α≤S≤Sst+α) or equal to or less than a predetermined value from the reference signal value Sst, the determination unit 22 determines that the radiation detecting element 7 from which the signal values S is read may be defective, failed or disconnected and regards it as a radiation detecting element 7A.

Pixels having abnormal signal values (defective pixels) should be preferably excluded. The defective pixels include those, for example, having values exceeding a predetermined signal value in a captured dark image or having differences in value between two captured dark images, but exclude pixels in a regular diagnostic image to be corrected.

A signal value S read from each radiation detecting element 7 may be varied in response to factors such as the temperature of the sensor panel SP. Instead of the reference signal value Sst set to a certain value or a function including only the variation (ΔV0−ΔV1) in the potential difference ΔV, a temperature sensor may be installed in, for example, the radiographic image capturing apparatus 1 and a function also including a temperature T measured by the temperature sensor as a variable may be provided to calculate the reference signal value Sst. This configuration allows the reference signal value Sst to be calculated in accordance with the temperature T of the radiographic image capturing apparatus 1.

Alternatively, signal values S read from the radiation detecting elements 7 may be plotted on a histogram to obtain a mode, median, dispersion σ2 or standard deviation σ, instead of installing a temperature sensor. The histogram allows the reference signal value Sst to be calculated based on the tendency or distribution of the signal values S.

Figure 12A:
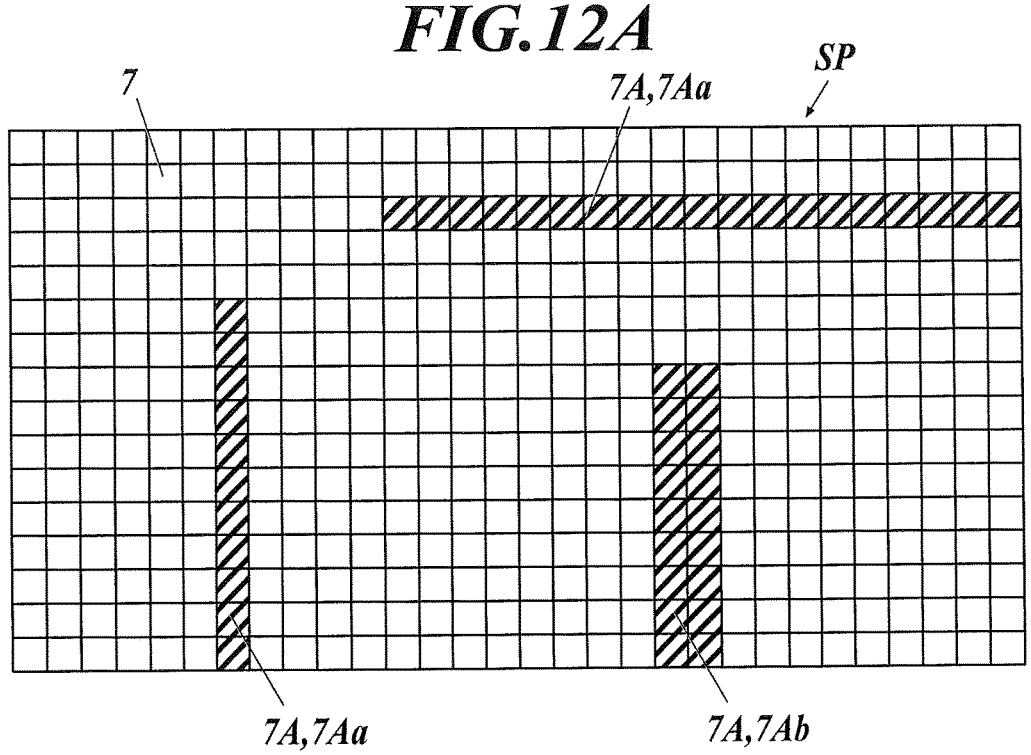
FIG. 12A illustrates line defects and a band defect on the sensor panel.

In the case of any disconnection of a single scanning line 5, signal line 6 or bias line 9, if disconnected radiation detecting elements 7A extend continuously, for example, the sensor panel SP in the direction remote from a readout circuit as shown in FIG. 12A, the determination unit 22 determines a signal line or a bias line to be broken (line defect). In contrast, if defective radiation detecting elements 7A extend continuously in the direction remote from the gate driver, the determination unit 22 determines a scanning line to be broken. For reticular bias lines, for example, if radiation detecting elements 7A do not extend continuously, the determination unit 22 determines a bias line or element in the radiation detecting element area to be abnormal or defective, thus successfully distinguishing it from a signal line disconnection.

Figure 12B:
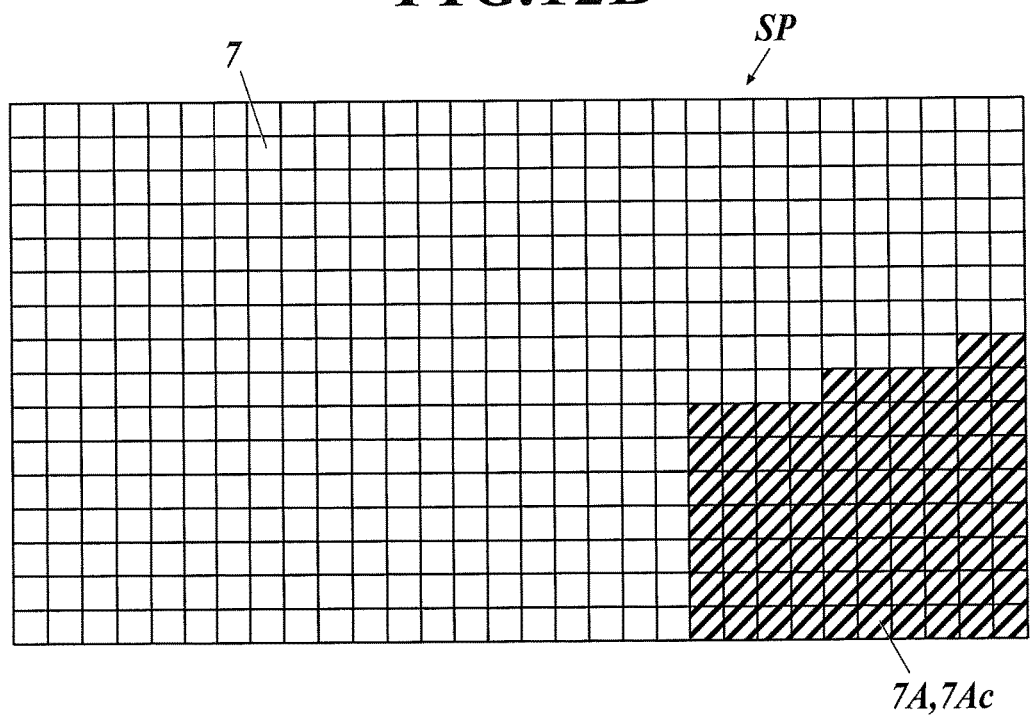
FIG. 12B illustrates a block defect on the sensor panel.

If a broken or cracked sensor substrate 4 (see FIG. 3), for example, results in disconnection of multiple scanning lines 5, signal lines 6 or bias lines 9, the determination unit 22 determines that defective radiation detecting elements extend continuously in adjacent rows on the sensor panel SP and that the sensor panel SP is broken or cracked, as shown in FIG. 12B. Any notice requesting an operator not to apply impact or load on the broken or cracked sensor substrate during replacement or repair facilitates repair and prevents propagation of cracks, leading to a reduction in downtime. In particular, once a crack forms, it propagates from the start point in the direction remote from the readout circuit and in the direction remote from the gate driver to form a characteristic L-shape. The L-shape crack provides a reference to determine disconnection of multiple scanning lines 5, signal lines 6 or bias lines 9 and/or breakage of the sensor substrate 4.

If radiation detecting elements 7A that may be disconnected extend in a row or form a block, the determination unit 22 according to this embodiment can determine that lines in the radiographic image capturing apparatus 1, such as the scanning lines 5, the signal lines 6 and the bias lines 9, are disconnected, which causes a defect in the sensor panel SP.

[Correction of Signal Values with Dark Image]

Each radiation detecting element 7 always has dark electric charge accumulated therein due to thermal excitation caused by heat generation (elevated temperature). The signal value S read, as shown above, has a dark image o superimposed thereon due to the dark electric charge. The determination process may be configured to perform the determination process with signal values Sa corrected by subtracting the values of dark images o from the signal values S, as shown in Expression (2):

$$Sa = S - o \tag{2}$$

In this case, the determination unit 22 reads a dark image o from each radiation detecting element 7 after reading signal values S as shown above, before performing a process to acquire the signal values S, or at factory shipping under the following conditions: No radiation is emitted, all the TFTs 8 are turned off, and the potential difference ΔV between each signal line 6 and the corresponding bias line 9 is kept at a constant potential difference ΔV0, for example, 5[V], in the readout process to read image data D from each radiation detecting elements 7 during a normal capture.

The determination unit 22 can be configured to correct the signal values S with read dark images o with Expression (2) and determine any defect in the sensor panel SP based on the

Third Embodiment

An embodiment of the radiographic image capturing system according to the present invention will now be described. In the first embodiment, the determination unit 22 of the radiographic image capturing apparatus 1, which functions as the controller 22, determines any defect in the sensor panel SP. Such determination may be performed by a console, for example. In the following description, the radiographic image capturing system is configured to determine the defect with the console.

In the following description, the determination process is performed by the console, which is a device displaying an image after arithmetic processing. Alternatively, the radiographic image capturing system may be configured to perform the determination process, for example, with a personal computer (PC) or a workstation (WS). In other words, a determination unit may be a console, PC or WS.

Figure 13:
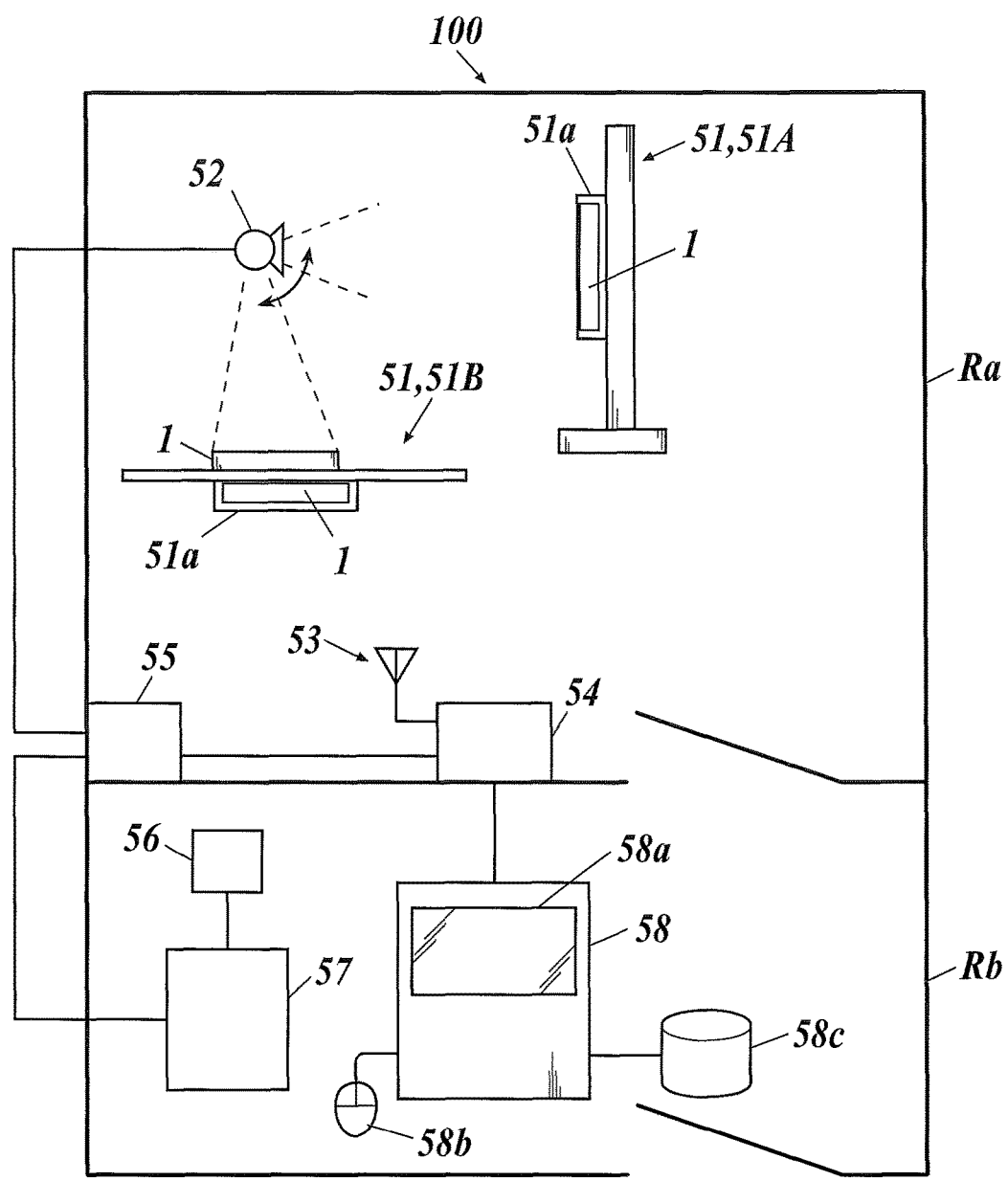
FIG. 13 illustrates a configuration of a radiographic image capturing system according to this embodiment.
Figure 14:
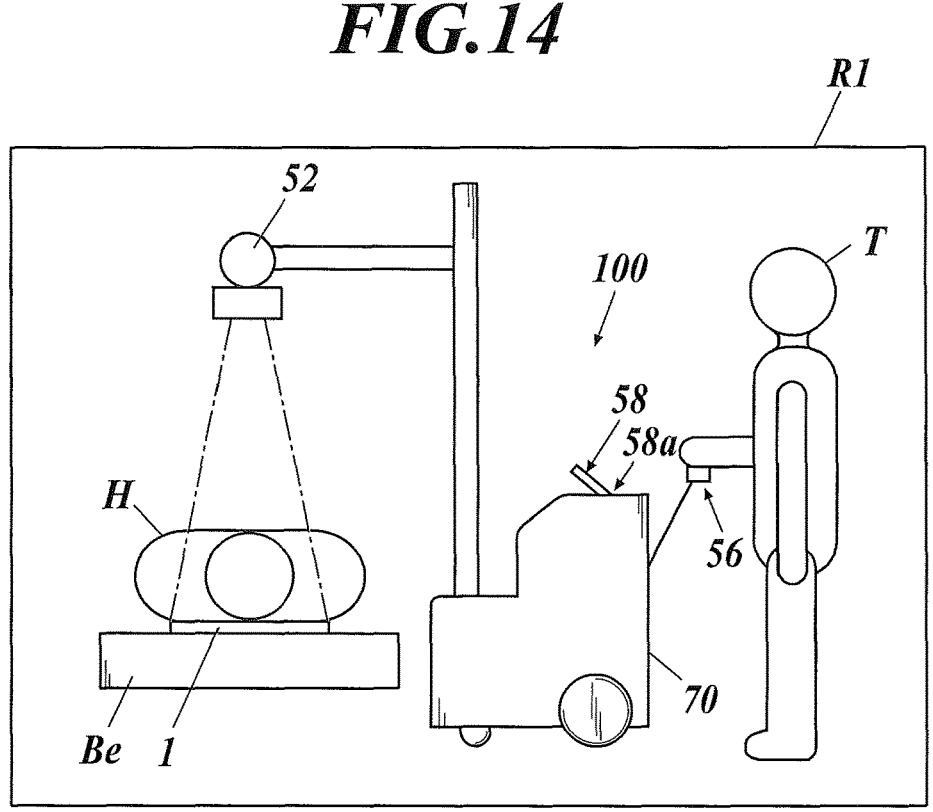
FIG. 14 illustrates another configuration of the radiographic image capturing system according to this embodiment.

A radiographic image capturing system 100 according to this embodiment will now be described. The radiographic image capturing system 100 may be installed in, for example, a capturing chamber Ra or a front chamber Rb, as shown in FIG. 13. Alternatively, the radiographic image capturing system 100 may be installed in a medical cart 70, as shown in FIG. 14.

For the radiographic image capturing system 100 installed in the capturing chamber Ra, the radiographic image capturing apparatus 1 may be placed in, for example, a cassette holder 51a of a capturing platform 51, as shown in FIG. 13. The capturing platform 51A in FIG. 13 represents a capturing platform used to image a standing subject. The capturing platform 51B represents a capturing platform used to image a lying subject. Alternatively, the radiographic image capturing apparatus 1 may be placed, for example, between a subject (not shown) lying on a top panel of the capturing platform 51B, which is used to image a lying subject, and the top panel.

The capturing chamber Ra is provided with at least one radiation generator 52, which emits radioactive rays. The capturing chamber Ra is also provided with a repeater 54 having an access point 53. The access point 53 relays communications between devices inside and outside the capturing chamber Ra through a wireless or wired network. The repeater 54 is connected to the generator 55 of the radiation generator 52 and a console 58 and relays communications between the radiographic image capturing apparatus 1 and the console 58 and between the generator 55 of the radiation generator 52 and the console 58.

The generator 55 of the radiation generator 52 controls the radiation generator 52 to emit radiation in a dose in proportion to an X-ray tube voltage, an X-ray tube current, or irradiation time (or mAs value) set by an operator or radiological technician.

The front chamber Rb (also referred to as an operation room) is provided with a console 57 of the radiation generator 52. The console 57 is provided with an exposure switch 56 which is manipulated by an operator, such as a radiological technician, to instruct the generator 55 to start emitting radioactivity. The front chamber Rb is also provided with the console 58 with a built-in computer. The console 58 may be installed outside the capturing chamber Ra and front chamber Rb or in any other chamber.

The console 58 is provided with a display 58a of a cathode ray tube (CRT) or liquid crystal display (LCD) and is connected to an input device 58b, such as a mouse or a keyboard. The console 58 is also connected to a storage unit 58c of a hard disk drive (HDD) or has a built-in storage unit 58c.

In contrast, the radiographic image capturing system 100 may include the medical cart 70 equipped with the radiation generator 52 and the console 58, as shown in FIG. 14. The medical cart 70 is moved to a medical ward R1 for capture. In this case, the generator 55 of the radiation generator 52 (not shown) and the repeater 54 are included in the medical cart 70.

In this case, the radiographic image capturing apparatus 1 is placed between a bed Be and a subject (patient) H, as shown in FIG. 14, or is applied to the body of the patient. In this case, an operator T, such as a radiological technician, also turns on the exposure switch 56 to emit radioactive rays from the radiation generator 52 to capture an image.

Figure 15:
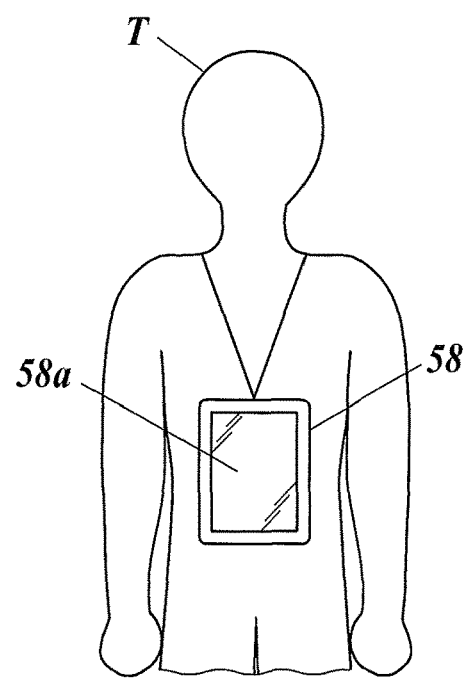
FIG. 15 illustrates an exemplary configuration of a portable console.

The console 58 may be a desk-top or lap-top computer, as shown in FIGS. 13 and 14. Alternatively, the console 58 may be, for example, a mobile terminal, as shown in FIG. 15, which is carried by the operator T, such as a radiological technician.

In the radiographic image capturing system 100 according to this embodiment, the controller 22 of the radiographic image capturing apparatus 1 reads signal values S from the radiation detecting elements 7 and sends the read signal values S to the console 58, as shown in FIG. 6. If the radiographic image capturing apparatus 1 is configured to read offset values o after reading the signal values S or before performing a process to acquire the signal values S, the controller 22 of the radiographic image capturing apparatus 1 sends the offset values o read from the radiation detecting elements 7 to the console 58.

The console 58 determines any defect in the sensor panel SP in the radiographic image capturing apparatus 1 based on the sent signal values S, as described in the first embodiment.

If the signal values S are corrected with the offset values o, the console 58 corrects the signal values S sent from the radiographic image capturing apparatus 1 with the dark images o with Expression (2) to obtain signal values Sa and then performs the determination process with the corrected signal values Sa. Alternatively, the dark images o, which are predetermined for the radiographic image capturing apparatus 1, may be stored in a storage unit 58c at factory shipping. Upon receipt of signal values S from the radiographic image capturing apparatus 1, the console reads the dark images o for the radiographic image capturing apparatus 1 from the storage unit 58c, corrects the sent signal values S by subtracting the values of the dark images o from the signal values S, as shown in Expression (2), and performs the determination process with the corrected signal values Sa.

As described above, the determination process performed by the console 58 can properly and correctly detect any disconnection in the lines in the radiographic image capturing apparatus 1, such as the scanning lines 5, the signal lines 6 and the bias lines 9, and thus properly and correctly determines any defect in the sensor panel SP of the radiographic image capturing apparatus 1. The third embodiment can provide the same advantageous effects as the first and second embodiments.

[Timing for Determination Process]

As described above, the console according to this embodiment can perform the determination process without emission of radiation to the radiographic image capturing apparatus 1. The radiographic image capturing apparatus 1 according to the first to third embodiments can read signal values S as shown above (see FIG. 6). The determination unit 22 (for the first and second embodiments) of the radiographic image capturing apparatus 1 and the console 58 (for the third embodiment) can perform the above determination process any time.

The above determination process may be configured to be performed, for example, regularly, at power-on of the radiographic image capturing apparatus 1, during charge of the built-in power supply 24 (see FIG. 4) in the radiographic image capturing apparatus 1, or during maintenance of the radiographic image capturing apparatus 1.

Alternatively, an acceleration sensor or a strain sensor, for example, may be installed in a panel that detects a predetermined acceleration (fall or impact) or panel distortion so that the determination process according to the present invention can be activated at the time of detection. Any disconnection in the scanning lines 5, the signal lines 6 and the bias lines 9 in the radiographic image capturing apparatus 1 is likely to occur when impact is applied to the radiographic image capturing apparatus 1, such as falling or hitting against other objects, as described above. To cope with this problem, a strain sensor capable of detecting distortion of the radiographic image capturing apparatus 1, an impact detector capable of detecting impact applied to the radiographic image capturing apparatus 1, and a fall detector, such as an acceleration sensor, capable of detecting a fall of the radiographic image capturing apparatus 1 (not shown), for example, are installed in the radiographic image capturing apparatus 1. The determination unit 22 or the console 58 in the radiographic image capturing apparatus 1 determines any defect in the sensor panel SP in the radiographic image capturing apparatus 1 when the strain sensor detects distortion of the radiographic image capturing apparatus 1, when the impact detector detects impact, or when the fall detector detects a fall of the radiographic image capturing apparatus 1.

This configuration allows the determination process to be performed properly when a line may be disconnected due to distortion of the radiographic image capturing apparatus 1, when any impact is applied to the radiographic image capturing apparatus 1, or when the radiographic image capturing apparatus 1 falls. Any defect in the sensor panel SP of the radiographic image capturing apparatus 1 due to a broken line can be determined promptly.

[Various Operations]

Various operations of the determination unit 22 (for the first and second embodiments) and the console 58 (for the third embodiment) of the radiographic image capturing apparatus 1 will now be described.

[Notice of any Defect in the Sensor Panel]

When the determination unit 22 or the console 58 of the radiographic image capturing apparatus 1 determines the sensor panel SP of the radiographic image capturing apparatus 1 to be defective, the determination unit 22 may be configured to, for example, illuminate or blink an indicator 40 of the radiographic image capturing apparatus 1 in a predetermined color, display letters or symbols, make a sound or provide an audible alert, or send a message on the display 58a of the console 58 to indicate the defect of the sensor panel SP of the radiographic image capturing apparatus 1. Alternatively, the determination unit 22 or the console 58 may be configured to notify the operator of the defect through sound or vibration.

This configuration allows the radiographic image capturing apparatus 1 to prompt a user or radiological technician to take appropriate measures, such as repair of the radiographic image capturing apparatus 1. This configuration can also effectively prevent the capture of an image with a defective radiographic image capturing apparatus 1 and thus can prevent re-capturing and the excess radiation exposition of the subject or patient during the re-capturing process.

[Correction of Radiation Image]

During the determination process, abnormal signal values S are read from the defective radiation detecting elements 7A shown in FIGS. 12A and 12B, which may be disconnected (hereinafter referred to as "disconnected elements 7A"). During the readout process in normal capturing, abnormal image data D is read from such disconnected elements 7A.

To cope with this problem, the radiographic image capturing apparatus 1 or the console 58 performs the following process on a radiation image generated based on the image data D read from each radiation detecting element 7 of the radiographic image capturing apparatus 1: The radiographic image capturing apparatus 1 or the console 58 discards the abnormal image data D read from the disconnected elements 7A for an image area, corresponding to the disconnected portion, of the generated radiation image, that is, a linear or block image area corresponding to the disconnected elements 7A, and then interpolates the image data D with normal image data D read from the surrounding radiation detecting elements 7 to correct the image, that is, create image data D for the disconnected elements 7A.

In case of disconnection of a single scanning line 5, signal line 6 or bias line 9, just like the disconnected elements 7Aa residing in a line (hereinafter referred to as a "line defect") shown in FIG. 12A, image data D read from the normal radiation detecting elements connected to the scanning lines 5 adjacent to the disconnected scanning line 5, that is, the normal radiation detecting elements 7 horizontally and/or vertically adjacent to the disconnected elements 7Aa shown in FIG. 12A, is used to correct the image.

In case of disconnection of two or more adjacent scanning lines 5 (hereinafter referred to as a "band defect"), just like the disconnected elements 7Ab shown in FIG. 12A, or in case of disconnected elements 7Ac forming a block (hereinafter referred to as a "block defect") shown in FIG. 12B, correction with the surrounding normal image data D, as described above, may create the following problem:

If the patient's affected area is captured with the portion having the band defect (disconnected elements 7Ab) or the block defect (disconnected elements 7Ac), of the sensor panel SP, the image correction involves the destruction of the abnormal image data D of the image area corresponding to the band defect or block defect and thus interpolation of the destructed image data D with the normal image data D of the surrounding area.

If the normal image data D of the surrounding area does not contain the patient's affected area, the image correction of the abnormal image data D of the image area corresponding to the band defect or block defect with the normal image data D results in a loss of patient's affected area that would be captured in the image area from the radiation image, in other words, the affected area cannot be captured in the radiation image.

If disconnected elements 7A reside in a line (i.e., a line defect) just like the disconnected elements 7Aa in FIG. 12A, the determination unit 22 or the console 58 of the radiographic image capturing apparatus 1 can correct the image as described above.

This configuration allows the radiographic image capturing apparatus 1 to be continuously used through an appropriate image correction for a line defect (disconnection of a single scanning line 5, a signal line or bias line 9), even if the determination process determines that the sensor panel SP is defective. In this case, the radiographic image capturing apparatus 1 may notify a user or radiological technician of the line defect to prompt the user or radiological technician to repair the radiographic image capturing apparatus 1 promptly.

If the disconnected elements 7A reside in two or more adjacent lines (i.e., a band defect) or form a block (i.e., a block defect), the determination unit 22 or the console 58 of the radiographic image capturing apparatus 1 may be configured so as not to perform image correction for the image area.

If there is an image area that cannot be corrected by the determination unit 22 or the console 58 of the radiographic image capturing apparatus 1, that is, an image area corresponding to the band defect (the disconnected elements 7Ab) in FIG. 12A or the block defect (the disconnected elements 7Ac) in FIG. 12B, the determination unit 22 or the console 58 of the radiographic image capturing apparatus 1 preferably notifies an operator that the radiographic image capturing apparatus 1 is unavailable.

This configuration effectively prevents the user or radiological technician from capturing an image with the defective radiographic image capturing apparatus 1 and urges the user to take appropriate measures, such as repair of the radiographic image capturing apparatus 1. In case of defect of a single pixel, which is handled as a point defect, the value of the defective pixel may be corrected with that of the surrounding pixels.

Figure 16:
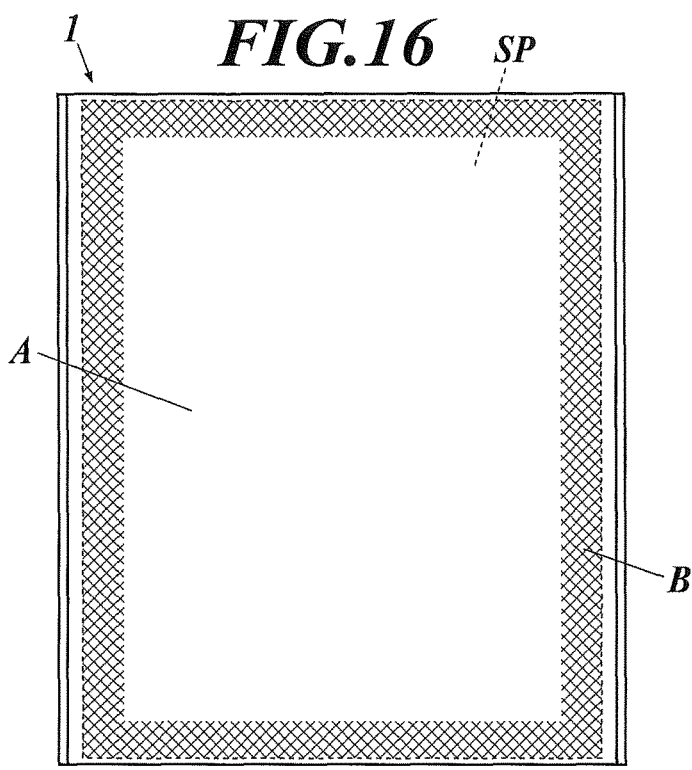
FIG. 16 illustrates the central and peripheral portions of the sensor panel of the radiographic image capturing apparatus.

When subject's or patient's affected area is captured with the radiographic image capturing apparatus 1, the radiographic image capturing apparatus 1 and the patient are positioned such that the center A of the sensor panel SP is aligned with the affected area, as shown in FIG. 16, in many cases. Accordingly, the patient's affected area is normally captured at or near the center of the captured radiation image.

If an image area which cannot be corrected resides in the periphery of the radiation image, in other words, the band defect (disconnected elements 7Ab) shown in FIG. 12A or the block defect (disconnected elements 7Ac) shown in FIG. 12B is in the periphery B of the sensor panel SP, capture of an image such that patient's affected area is not aligned with the band defect or block defect allows patient's affected area to be within the radiation image. FIG. 16 shows the periphery B of the sensor panel SP as a hatched area. This does not indicate the band defect or block defect is in the entire periphery B of the sensor panel SP.

If an image area which cannot be corrected resides in the periphery of a radiation image, in other words, the band defect or block defect is in the periphery B of the sensor panel SP of the radiographic image capturing apparatus 1, a portion other than the band defect or block defect corresponding to the image area which cannot be corrected, on the sensor panel SP can be used to capture an image. Thus, the determination unit 22 or the console 58 of the radiographic image capturing apparatus 1 may be configured to notify the operator of such possible operation.

Figure 17:
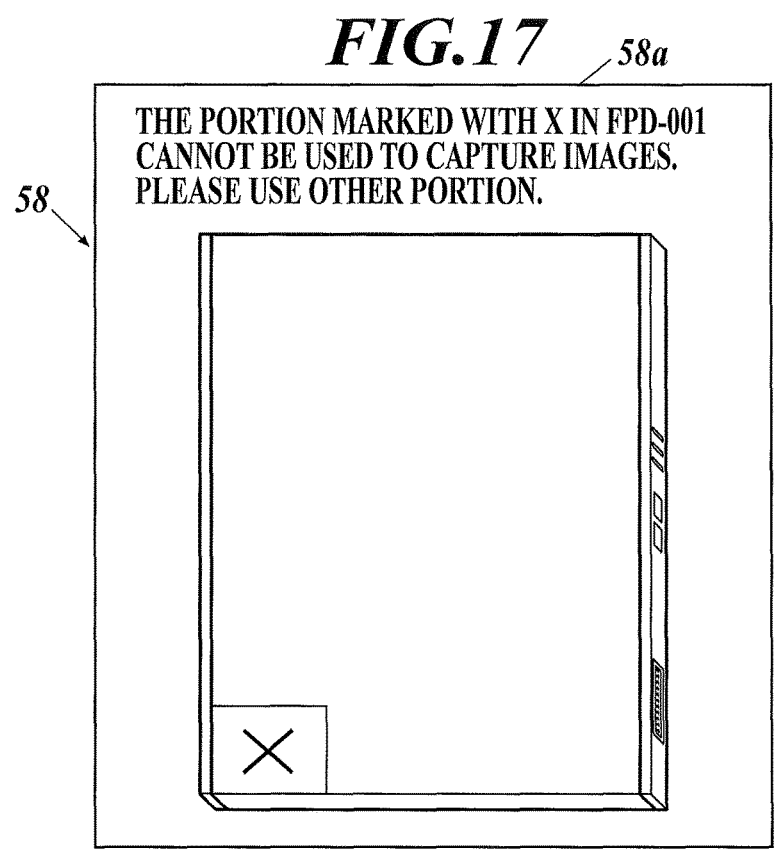
FIG. 17 shows an exemplary message to instruct users to use a portion other than an unusable portion of the radiographic image capturing apparatus for capture.

Such notification may be provided, for example, in the form of a message displayed on the display 58a of the console 58 shown in FIG. 17, a mark "x", or a predetermined color (for example, red). More specifically, such as mark or color is affixed on the portion, having the band defect or block defect, on the schematically illustrated radiographic image capturing apparatus 1, that is, a portion not capable of capturing an image (or the image area which cannot be corrected) to indicate that an operator should use any portion other than the marked or colored portion.

This configuration allows the user or radiological technician to properly recognize the necessity for repair of the radiographic image capturing apparatus 1 and continuously capture an image with a portion capable of capturing an image on the sensor panel SP of the radiographic image capturing apparatus 1 until the operator takes appropriate measures, such as repair of the radiographic image capturing apparatus 1.

[Notice to Service Center]

The determination unit 22 or the console 58 of the radiographic image capturing apparatus 1 may be configured to provide the results of the determination process as shown below not only to the user or radiological technician but also to a service center and a device administrator of the facility (or hospital): The sensor panel SP of the radiographic image capturing apparatus 1 is defective, the sensor panel SP has a line defect, or the sensor panel SP has a band or block defect, which precludes the use of the radiographic image capturing apparatus 1.

This configuration allows the service center and the device administrator of the facility to know that the sensor panel SP of the radiographic image capturing apparatus 1 is determined to be defected without delay and respond to the defect promptly, such as informing the user of the fact promptly, arranging to repair the radiographic image capturing apparatus 1 or procuring a new sensor panel SP for replace.

The determination unit 22 or the console 58 of the radiographic image capturing apparatus 1 can be configured to notify a service center of a minor defect for a correctable image area (i.e., a line defect) or notify the service center or the device administrator of the facility of a major defect, i.e., a failure for an image area which cannot be corrected (i.e., a band or block defect).

Any major defect in the sensor panel SP of the radiographic image capturing apparatus 1 must be solved more promptly than any minor correctable defect. The above configuration allows the service center and the device administrator of the facility to respond quickly to the major defect in the sensor panel SP and can effectively avoid a situation that precludes the capturing of an image by, for example, procuring a replacement radiographic image capturing apparatus 1 to replace promptly.

It should be understood that the embodiments described above are not construed to limit the present invention and can be appropriately modified without departing from the scope of the present invention.

What is claimed is:

1. A radiographic image capturing apparatus, comprising:
a sensor panel including scanning lines, signal lines, a two-dimensional array of radiation detecting elements each having a first electrode and a second electrode, bias lines each applying a reverse bias voltage to the corresponding radiation detecting element, and switching elements, the first electrode of each radiation detecting element being connected to the corresponding bias line, the second electrode of the radiation detecting element being connected to the corresponding signal line via the corresponding switching element; and
a determination unit determining any defect in the sensor panel, wherein
the determination unit reads a signal value before and after varying a potential difference between each signal line and the corresponding bias line, and determines any defect in the sensor panel based on the difference of the read signal values.

2. The radiographic image capturing apparatus according to claim 1, wherein the determination unit varies at least one of the reverse bias voltage and a signal line voltage between a reset process of the radiation detecting elements and a readout process of the signal value to vary a potential difference between each signal line and the corresponding bias line.

3. The radiographic image capturing apparatus according to claim 1, wherein the determination unit varies at least one of a signal line voltage and a bias line voltage to increase a potential difference between each signal line and the corresponding bias line.

4. The radiographic image capturing apparatus according to claim 1, wherein the determination unit corrects the signal value with a dark image and determines any defect in the sensor panel based on the corrected signal value.

5. The radiographic image capturing apparatus according to claim 1, further comprising at least one of a strain sensor detecting distortion of the radiographic image capturing apparatus, an impact detector detecting impact applied to the radiographic image capturing apparatus and a fall detector detecting a fall of the radiographic image capturing apparatus, wherein
the determination unit determines any defect in the sensor panel when the strain sensor detects distortion of the radiographic image capturing apparatus, when the impact detector detects impact, or when the fall detector detects a fall of the radiographic image capturing apparatus.

6. The radiographic image capturing apparatus according to claim 1, wherein the determination unit notifies an operator of a defect when the determination unit determines that there is the defect in the sensor panel.

7. The radiographic image capturing apparatus according to claim 1, wherein
the determination unit determines whether there is a line disconnection in the scanning lines, the signal lines, or the bias lines, and
if the determination unit determines there is the line disconnection, the determination unit performs image correction on a correctable image area, the image area corresponding to a disconnected portion, the image area residing in a radiation image generated from image data read from each radiation detecting element.

8. The radiographic image capturing apparatus according to claim 7, wherein the determination unit notifies that the radiographic image capturing apparatus is unavailable if the image area cannot be corrected.

9. The radiographic image capturing apparatus according to claim 8, wherein if the image area which cannot be corrected resides in a periphery of the radiation image, the determination unit notifies that a portion other than a portion corresponding to the image area which cannot be corrected on the sensor panel can be used to capture an image.

10. The radiographic image capturing apparatus according to claim 7, wherein the determination unit notifies a service center and a device administrator of a facility of a minor defect for the correctable image area or a major defect for the image area which cannot be corrected.

11. A radiographic image capturing system, comprising:
a radiographic image capturing apparatus including a sensor panel provided with scanning lines, signal lines, a two-dimensional array of radiation detecting elements each having a first electrode and a second electrode, bias lines each applying a reverse bias voltage to the corresponding radiation detecting element, and switching elements, the first electrode of each radiation detecting element being connected to the corresponding bias line, the second electrode of the radiation detecting element being connected to the corresponding signal line via the corresponding switching element; and
a determination unit determining any defect in the sensor panel of the radiographic image capturing apparatus, wherein
the determination unit reads a signal value before and after varying a potential difference between each signal line and the corresponding bias line, and determines any defect in the sensor panel based on the difference of the read signal values.

* * * * *